(12) United States Patent
Eldridge et al.

(10) Patent No.: US 10,265,450 B2
(45) Date of Patent: Apr. 23, 2019

(54) MULTIAXIAL CONNECTOR FOR IMPLANTABLE DEVICES

(71) Applicant: TC1 LLC, St. Paul, MN (US)

(72) Inventors: David Eldridge, Brentwood, CA (US); Joseph C. Stark, III, San Leandro, CA (US); Andrew MacDonell, Pleasanton, CA (US); Scott Kramer, Pleasanton, CA (US); Thomas George Kilavos, Pleasanton, CA (US); Fabian Frigon Franco, Livermore, CA (US)

(73) Assignee: TC1 LLC, St. Paul, MN (US)

( * ) Notice: Subject to any disclaimer, the term of this patent is extended or adjusted under 35 U.S.C. 154(b) by 0 days.

(21) Appl. No.: 15/408,545

(22) Filed: Jan. 18, 2017

(65) Prior Publication Data

US 2017/0119947 A1  May 4, 2017

Related U.S. Application Data

(62) Division of application No. 14/876,554, filed on Oct. 6, 2015, now Pat. No. 9,583,874.

(Continued)

(51) Int. Cl.
*A61M 1/00* (2006.01)
*A61M 1/12* (2006.01)
(Continued)

(52) U.S. Cl.
CPC .............. *A61M 1/122* (2014.02); *A61M 1/12* (2013.01); *A61M 1/127* (2013.01); *H01F 38/14* (2013.01); *H01R 4/302* (2013.01); *H01R 13/03* (2013.01); *H01R 13/521* (2013.01); *H01R 13/5224* (2013.01); *H01R 13/629* (2013.01); *H01R 13/639* (2013.01); *H01R 13/641* (2013.01);
(Continued)

(58) Field of Classification Search
CPC ..................................................... A61M 1/122
See application file for complete search history.

(56) References Cited

U.S. PATENT DOCUMENTS

| 4,041,955 A | 8/1977 | Kelly et al. |
| 4,352,960 A | 10/1982 | Dormer et al. |

(Continued)

FOREIGN PATENT DOCUMENTS

| DE | 202012000166 U1 | 6/2013 |
| DE | 102012201073 A1 | 7/2013 |

(Continued)

OTHER PUBLICATIONS

Bonde et al.; Promise of unrestricted mobility with innovative, portable wireless powering of a mechanical circulatory assist device; American Association for Thoracic Surgery; © 2012; 2 pgs.; retrieved Mar. 12, 2014 from the internet: http://aats.org/annualmeeting/Abstracts/2012/T8.cgi.

(Continued)

*Primary Examiner* — Eric D. Bertram
(74) *Attorney, Agent, or Firm* — Armstrong Teasdale LLP

(57) ABSTRACT

Disclosed are systems for wireless energy transfer including transcutaneous energy transfer. Embodiments are disclosed for electrical connections between an implanted wireless receiver and an implanted medical device powered by the receiver. Methods for manufacturing and using the devices and system are also disclosed.

12 Claims, 18 Drawing Sheets

Related U.S. Application Data

(60) Provisional application No. 62/060,435, filed on Oct. 6, 2014.

(51) Int. Cl.

| | | |
|---|---|---|
| *H01F 38/14* | (2006.01) | |
| *H01R 13/52* | (2006.01) | |
| *H01R 13/639* | (2006.01) | |
| *H02J 50/10* | (2016.01) | |
| *H01R 13/03* | (2006.01) | |
| *H01R 13/629* | (2006.01) | |
| *H01R 13/641* | (2006.01) | |
| *H01R 4/30* | (2006.01) | |
| H01R 105/00 | (2006.01) | |
| A61M 1/10 | (2006.01) | |

(52) U.S. Cl.
CPC .............. *H02J 50/10* (2016.02); *A61M 1/101* (2013.01); *A61M 1/1008* (2014.02); *A61M 2205/04* (2013.01); *A61M 2205/8243* (2013.01); *H01R 2105/00* (2013.01); *H01R 2201/12* (2013.01)

(56) References Cited

U.S. PATENT DOCUMENTS

| | | |
|---|---|---|
| 4,561,443 A | 12/1985 | Hogrefe et al. |
| 4,561,444 A | 12/1985 | Livingston et al. |
| 4,630,615 A | 12/1986 | Yomtov |
| 4,679,560 A | 7/1987 | Galbraith |
| 4,726,378 A | 2/1988 | Kaplan |
| 4,736,747 A | 4/1988 | Drake |
| 4,924,171 A | 5/1990 | Baba et al. |
| 4,945,305 A | 7/1990 | Blood |
| 5,070,223 A | 12/1991 | Colasante |
| 5,346,458 A | 9/1994 | Affeld |
| 5,350,413 A | 9/1994 | Miller et al. |
| 5,569,156 A | 10/1996 | Mussivand |
| 5,630,836 A | 5/1997 | Prem et al. |
| 5,690,693 A | 11/1997 | Wang et al. |
| 5,702,431 A | 12/1997 | Wang et al. |
| 5,755,748 A | 5/1998 | Borza |
| 5,771,438 A | 6/1998 | Palermo et al. |
| 5,831,248 A | 11/1998 | Hojyo et al. |
| 5,948,006 A | 9/1999 | Mann |
| 6,123,726 A | 9/2000 | Mori et al. |
| 6,149,683 A | 11/2000 | Lancisi et al. |
| 6,212,430 B1 | 4/2001 | Kung |
| 6,296,533 B1 | 10/2001 | Grubbs et al. |
| 6,312,338 B1 | 11/2001 | Sato et al. |
| 6,320,354 B1 | 11/2001 | Sengupta et al. |
| 6,324,431 B1 | 11/2001 | Zarinetchi et al. |
| 6,327,504 B1 | 12/2001 | Dolgin et al. |
| 6,389,318 B1 | 5/2002 | Zarinetchi et al. |
| 6,400,991 B1 | 6/2002 | Kung |
| 6,442,434 B1 | 8/2002 | Zarinetchi et al. |
| 6,451,055 B1 | 9/2002 | Weiss |
| 6,458,164 B1 | 10/2002 | Weiss |
| 6,478,820 B1 | 11/2002 | Weiss |
| 6,553,263 B1 | 4/2003 | Meadows et al. |
| 6,579,315 B1 | 6/2003 | Weiss |
| 6,591,139 B2 | 7/2003 | Loftin et al. |
| 6,605,032 B2 | 8/2003 | Benkowski et al. |
| 6,647,298 B2 | 11/2003 | Abrahamson et al. |
| 6,650,213 B1 | 11/2003 | Sakurai et al. |
| 6,723,039 B2 | 4/2004 | French et al. |
| 6,772,011 B2 | 8/2004 | Dolgin |
| 6,801,807 B2 | 10/2004 | Abrahamson |
| 6,810,289 B1 | 10/2004 | Shaquer |
| 6,850,803 B1 | 2/2005 | Jimenez et al. |
| 6,894,456 B2 | 5/2005 | Tsukamoto et al. |
| 6,895,281 B1 | 5/2005 | Amundson et al. |
| 6,949,065 B2 | 9/2005 | Sporer et al. |
| 6,960,968 B2 | 11/2005 | Odenaal et al. |
| 6,967,621 B1 | 11/2005 | Cadotte, Jr. et al. |
| 6,985,773 B2 | 1/2006 | Von Arx et al. |
| 7,015,769 B2 | 3/2006 | Schulman et al. |
| 7,107,103 B2 | 9/2006 | Schulman et al. |
| 7,126,310 B1 | 10/2006 | Barron |
| 7,225,032 B2 | 5/2007 | Schmeling et al. |
| 7,246,040 B2 | 7/2007 | Borg et al. |
| 7,286,880 B2 | 10/2007 | Olson et al. |
| 7,428,438 B2 | 9/2008 | Parramon et al. |
| 7,471,986 B2 | 12/2008 | Hatlestad |
| 7,496,733 B2 | 2/2009 | Altman et al. |
| 7,505,816 B2 | 3/2009 | Schmeling et al. |
| 7,515,012 B2 | 4/2009 | Schulman et al. |
| 7,522,878 B2 | 4/2009 | Baarman |
| 7,532,901 B1 | 5/2009 | Lafranchise et al. |
| 7,565,187 B1 | 7/2009 | Dynok et al. |
| 7,571,007 B2 | 8/2009 | Erickson et al. |
| 7,574,173 B2 | 8/2009 | Terranova et al. |
| 7,587,241 B2 | 9/2009 | Parramon et al. |
| 7,599,743 B2 | 10/2009 | Hassler, Jr. et al. |
| 7,650,187 B2 | 1/2010 | Gruber et al. |
| 7,650,192 B2 | 1/2010 | Wahlstrand |
| 7,711,433 B2 | 5/2010 | Davis et al. |
| 7,720,546 B2 | 5/2010 | Ginggen et al. |
| 7,741,734 B2 | 6/2010 | Joannopoulos |
| 7,761,164 B2 | 7/2010 | Verhoef et al. |
| 7,774,069 B2 | 8/2010 | Olson et al. |
| 7,782,190 B1 | 8/2010 | Martin et al. |
| 7,805,200 B2 | 9/2010 | Kast et al. |
| 7,812,481 B2 | 10/2010 | Iisaka et al. |
| 7,818,036 B2 | 10/2010 | Lair et al. |
| 7,818,037 B2 | 10/2010 | Lair et al. |
| 7,825,543 B2 | 11/2010 | Karalis et al. |
| 7,830,114 B2 | 11/2010 | Reed |
| 7,865,245 B2 | 1/2011 | Torgerson et al. |
| 7,872,367 B2 | 1/2011 | Recksiek et al. |
| 7,904,170 B2 | 3/2011 | Harding |
| 7,932,696 B2 | 4/2011 | Peterson et al. |
| 7,962,222 B2 | 6/2011 | He et al. |
| RE42,682 E | 9/2011 | Barreras et al. |
| 8,076,807 B2 | 12/2011 | Bohn et al. |
| 8,081,925 B2 | 12/2011 | Parramon et al. |
| 8,096,954 B2 | 1/2012 | Stahmann et al. |
| 8,140,168 B2 | 3/2012 | Olson et al. |
| 8,150,529 B2 | 4/2012 | Snell et al. |
| 8,165,694 B2 | 4/2012 | Carbunaru et al. |
| 8,185,212 B2 | 5/2012 | Carbunaru et al. |
| 8,193,766 B2 | 6/2012 | Rondoni et al. |
| 8,203,434 B2 | 6/2012 | Yoshida |
| 8,244,367 B2 | 8/2012 | Wahlstrand et al. |
| 8,247,926 B2 | 8/2012 | Issa et al. |
| 8,258,653 B2 | 9/2012 | Kitamura et al. |
| 8,265,770 B2 | 9/2012 | Toy et al. |
| 8,278,784 B2 | 10/2012 | Cook et al. |
| 8,292,052 B2 | 10/2012 | Bohori et al. |
| 8,299,652 B2 | 10/2012 | Smith et al. |
| 8,301,079 B2 | 10/2012 | Baarman |
| 8,319,473 B2 | 11/2012 | Choi et al. |
| 8,362,742 B2 | 1/2013 | Kallmyer |
| 8,373,310 B2 | 2/2013 | Baarman et al. |
| 8,378,522 B2 | 2/2013 | Cook et al. |
| 8,378,523 B2 | 2/2013 | Cook et al. |
| 8,463,395 B2 | 6/2013 | Forsell |
| 8,489,200 B2 | 7/2013 | Zarinetchi et al. |
| 8,551,163 B2 | 10/2013 | Aber et al. |
| 8,562,508 B2 | 10/2013 | Dague et al. |
| 8,581,793 B2 | 11/2013 | Carr |
| 8,587,154 B2 | 11/2013 | Fells et al. |
| 8,620,447 B2 | 12/2013 | D'Ambrosio et al. |
| 8,628,460 B2 | 1/2014 | Yomtov et al. |
| 8,629,578 B2 | 1/2014 | Kurs et al. |
| 8,668,473 B2 | 3/2014 | Larose et al. |
| 8,694,117 B2 | 4/2014 | Aghassian et al. |
| 8,810,071 B2 | 8/2014 | Sauerlaender et al. |
| 8,884,468 B2 | 11/2014 | Lemmens et al. |
| 8,909,351 B2 | 12/2014 | Dinsmoor et al. |
| 8,971,958 B2 | 3/2015 | Frikart et al. |
| 9,002,468 B2 | 4/2015 | Shea et al. |
| 9,106,083 B2 | 8/2015 | Partovi |

(56) References Cited

U.S. PATENT DOCUMENTS

| | | |
|---|---|---|
| 9,192,704 B2 | 11/2015 | Yomtov et al. |
| 9,302,093 B2 | 4/2016 | Mashiach |
| 9,515,494 B2 | 12/2016 | Kurs et al. |
| 9,515,495 B2 | 12/2016 | Kurs et al. |
| 9,560,787 B2 | 1/2017 | Kallmyer et al. |
| 2002/0038138 A1 | 3/2002 | Zarinetchi et al. |
| 2002/0087204 A1 | 7/2002 | Kung et al. |
| 2002/0093456 A1 | 7/2002 | Sawamura et al. |
| 2003/0171792 A1 | 9/2003 | Zarinetchi et al. |
| 2004/0138725 A1 | 7/2004 | Forsell |
| 2004/0256146 A1 | 12/2004 | Frericks et al. |
| 2005/0006083 A1 | 1/2005 | Chen et al. |
| 2005/0090883 A1 | 4/2005 | Westlund et al. |
| 2005/0288743 A1 | 12/2005 | Ahn et al. |
| 2006/0199997 A1 | 9/2006 | Hassler et al. |
| 2006/0271129 A1 | 11/2006 | Tai et al. |
| 2007/0096686 A1 | 5/2007 | Jimenez et al. |
| 2007/0123948 A1 | 5/2007 | Dal Molin |
| 2007/0142696 A1 | 6/2007 | Crosby et al. |
| 2007/0191706 A1 | 8/2007 | Calderon et al. |
| 2008/0009198 A1 | 1/2008 | Marino |
| 2008/0027293 A1 | 1/2008 | Vodermayer et al. |
| 2008/0054638 A1 | 3/2008 | Greene et al. |
| 2008/0100294 A1 | 5/2008 | Rohling et al. |
| 2008/0149736 A1 | 6/2008 | Kim et al. |
| 2008/0167531 A1 | 7/2008 | McDermott |
| 2008/0211320 A1 | 9/2008 | Cook et al. |
| 2009/0018616 A1 | 1/2009 | Quick et al. |
| 2009/0051224 A1 | 2/2009 | Cook et al. |
| 2009/0072628 A1 | 3/2009 | Cook et al. |
| 2009/0081943 A1 | 3/2009 | Dobyns et al. |
| 2009/0174264 A1 | 7/2009 | Onishi et al. |
| 2009/0212736 A1 | 8/2009 | Baarman et al. |
| 2009/0226328 A1 | 9/2009 | Morello |
| 2009/0270679 A1 | 10/2009 | Hoeg et al. |
| 2009/0284220 A1 | 11/2009 | Toncich et al. |
| 2010/0019985 A1 | 1/2010 | Bashyam et al. |
| 2010/0033021 A1 | 2/2010 | Bennett |
| 2010/0035453 A1 | 2/2010 | Tronnes et al. |
| 2010/0045114 A1 | 2/2010 | Sample et al. |
| 2010/0063347 A1 | 3/2010 | Yomtov et al. |
| 2010/0066305 A1 | 3/2010 | Takahashi et al. |
| 2010/0069992 A1 | 3/2010 | Aghassian et al. |
| 2010/0109958 A1 | 5/2010 | Haubrich et al. |
| 2010/0114143 A1 | 5/2010 | Albrecht et al. |
| 2010/0122995 A1 | 5/2010 | Thomas et al. |
| 2010/0171368 A1 | 7/2010 | Schatz et al. |
| 2010/0184371 A1 | 7/2010 | Cook et al. |
| 2010/0194334 A1 | 8/2010 | Kirby et al. |
| 2010/0210233 A1 | 8/2010 | Cook et al. |
| 2010/0211134 A1 | 8/2010 | Forsell |
| 2010/0222848 A1 | 9/2010 | Forsell |
| 2010/0222849 A1 | 9/2010 | Forsell |
| 2010/0225174 A1 | 9/2010 | Jiang |
| 2010/0244576 A1 | 9/2010 | Hillan et al. |
| 2010/0253340 A1 | 10/2010 | Corum et al. |
| 2010/0256708 A1 | 10/2010 | Thornton et al. |
| 2010/0277121 A1 | 11/2010 | Hall et al. |
| 2010/0308939 A1 | 12/2010 | Kurs |
| 2010/0314946 A1 | 12/2010 | Budde et al. |
| 2010/0331919 A1 | 12/2010 | Digiore et al. |
| 2011/0025132 A1 | 2/2011 | Sato |
| 2011/0043050 A1 | 2/2011 | Yabe et al. |
| 2011/0046699 A1 | 2/2011 | Mazanec |
| 2011/0101790 A1 | 5/2011 | Budgett |
| 2011/0109263 A1 | 5/2011 | Sakoda et al. |
| 2011/0115431 A1 | 5/2011 | Dunworth et al. |
| 2011/0127848 A1 | 6/2011 | Ryu et al. |
| 2011/0148215 A1 | 6/2011 | Marzetta et al. |
| 2011/0178361 A1 | 7/2011 | Yomtov |
| 2011/0181235 A1 | 7/2011 | Walley et al. |
| 2011/0205083 A1 | 8/2011 | Janna et al. |
| 2011/0234155 A1 | 9/2011 | Chen et al. |
| 2011/0241436 A1 | 10/2011 | Furukawa |
| 2011/0245892 A1 | 10/2011 | Kast et al. |
| 2011/0266880 A1 | 11/2011 | Kim et al. |
| 2011/0276110 A1 | 11/2011 | Whitehurst et al. |
| 2011/0278948 A1 | 11/2011 | Forsell |
| 2011/0291489 A1 | 12/2011 | Tsai et al. |
| 2011/0291613 A1 | 12/2011 | Rosik et al. |
| 2011/0295345 A1 | 12/2011 | Wells et al. |
| 2011/0298294 A1 | 12/2011 | Takada et al. |
| 2011/0301667 A1 | 12/2011 | Olson et al. |
| 2011/0313238 A1 | 12/2011 | Reichenbach et al. |
| 2012/0001485 A1 | 1/2012 | Uchida |
| 2012/0032522 A1 | 2/2012 | Schatz et al. |
| 2012/0039102 A1 | 2/2012 | Shinoda |
| 2012/0057322 A1 | 3/2012 | Waffenschmidt |
| 2012/0065458 A1 | 3/2012 | Tol |
| 2012/0080957 A1 | 4/2012 | Cooper et al. |
| 2012/0091951 A1 | 4/2012 | Sohn |
| 2012/0104997 A1 | 5/2012 | Carobolante |
| 2012/0109256 A1 | 5/2012 | Meskins et al. |
| 2012/0119914 A1 | 5/2012 | Uchida |
| 2012/0146575 A1 | 6/2012 | Armstrong et al. |
| 2012/0149229 A1 | 6/2012 | Kearsley et al. |
| 2012/0150259 A1 | 6/2012 | Meskens |
| 2012/0153739 A1 | 6/2012 | Cooper et al. |
| 2012/0153954 A1 | 6/2012 | Ota et al. |
| 2012/0157753 A1 | 6/2012 | D'Ambrosio |
| 2012/0157754 A1 | 6/2012 | D'Ambrosio |
| 2012/0158407 A1 | 6/2012 | Forsell |
| 2012/0161539 A1 | 6/2012 | Kim et al. |
| 2012/0164943 A1 | 6/2012 | Bennett |
| 2012/0169132 A1 | 7/2012 | Choudhary et al. |
| 2012/0169133 A1 | 7/2012 | Lisi et al. |
| 2012/0169137 A1 | 7/2012 | Lisi et al. |
| 2012/0169139 A1 | 7/2012 | Kudo |
| 2012/0169278 A1 | 7/2012 | Choi et al. |
| 2012/0175967 A1 | 7/2012 | Dibben et al. |
| 2012/0235364 A1 | 9/2012 | Wang et al. |
| 2012/0239118 A1 | 9/2012 | Ozawa et al. |
| 2012/0245649 A1 | 9/2012 | Bohori et al. |
| 2012/0245664 A1 | 9/2012 | Smith et al. |
| 2012/0259398 A1 | 10/2012 | Chen et al. |
| 2012/0274148 A1 | 11/2012 | Sung et al. |
| 2012/0306433 A1 | 12/2012 | Kim et al. |
| 2013/0007949 A1 | 1/2013 | Kurs et al. |
| 2013/0060103 A1 | 3/2013 | Bergida et al. |
| 2013/0119773 A1 | 5/2013 | Davis |
| 2013/0127253 A1 | 5/2013 | Stark et al. |
| 2013/0149960 A1 | 6/2013 | Dec et al. |
| 2013/0159956 A1 | 6/2013 | Verghese et al. |
| 2013/0190551 A1* | 7/2013 | Callaway ............ A61M 1/127 600/16 |
| 2013/0197607 A1 | 8/2013 | Wilder et al. |
| 2013/0214731 A1 | 8/2013 | Dinsmoor |
| 2013/0241306 A1 | 9/2013 | Aber et al. |
| 2013/0241468 A1 | 9/2013 | Moshfeghi |
| 2013/0271088 A1 | 10/2013 | Hwang et al. |
| 2013/0289334 A1 | 10/2013 | Badstibner et al. |
| 2013/0310630 A1 | 11/2013 | Smith et al. |
| 2013/0320773 A1 | 12/2013 | Schatz et al. |
| 2013/0331638 A1 | 12/2013 | Cameron et al. |
| 2014/0005466 A1 | 1/2014 | Crosby et al. |
| 2014/0011447 A1 | 1/2014 | Konanur et al. |
| 2014/0028110 A1 | 1/2014 | Petersen et al. |
| 2014/0028111 A1 | 1/2014 | Hansen et al. |
| 2014/0031606 A1 | 1/2014 | Hansen et al. |
| 2014/0152252 A1 | 6/2014 | Wood |
| 2014/0163644 A1 | 6/2014 | Scott et al. |
| 2014/0265620 A1 | 9/2014 | Hoarau et al. |
| 2014/0265621 A1 | 9/2014 | Wong et al. |
| 2014/0275727 A1 | 9/2014 | Bonde et al. |
| 2015/0123654 A1 | 5/2015 | Gagnon et al. |
| 2015/0207330 A1 | 7/2015 | Petersen |
| 2015/0207331 A1 | 7/2015 | Petersen |
| 2015/0222127 A1 | 8/2015 | Hansen |
| 2015/0222128 A1 | 8/2015 | Hansen |
| 2015/0222139 A1 | 8/2015 | Petersen et al. |
| 2015/0229289 A1 | 8/2015 | Suzuki |
| 2015/0290373 A1 | 10/2015 | Rudser et al. |
| 2016/0135684 A1 | 5/2016 | Kappel et al. |
| 2016/0218432 A1 | 7/2016 | Pope et al. |

(56) References Cited

U.S. PATENT DOCUMENTS

| | | |
|---|---|---|
| 2016/0250484 A1 | 9/2016 | Nguyen et al. |
| 2016/0254703 A1 | 9/2016 | Hansen |
| 2016/0254704 A1 | 9/2016 | Hansen et al. |

FOREIGN PATENT DOCUMENTS

| | | |
|---|---|---|
| EP | 0589608 A2 | 9/1993 |
| EP | 1513241 A1 | 3/2005 |
| EP | 2267864 A2 | 6/2010 |
| GB | 2477034 A | 7/2011 |
| JP | H03109063 A | 5/1991 |
| JP | 11-506646 | 6/1999 |
| JP | 2013094456 A | 5/2013 |
| JP | 2013161640 A | 8/2013 |
| JP | 2014160611 A | 9/2014 |
| KR | 1020020089605 | 11/2002 |
| KR | 1020120077448 | 7/2012 |
| KR | 1020120007296 | 10/2012 |
| WO | 0001442 A2 | 1/2000 |
| WO | 0074747 A1 | 12/2000 |
| WO | 0137926 A1 | 5/2001 |
| WO | 2005106901 A2 | 11/2005 |
| WO | 2007053881 A1 | 5/2007 |
| WO | 2008066941 A2 | 6/2008 |
| WO | 2009018271 A1 | 2/2009 |
| WO | 2009021220 A1 | 2/2009 |
| WO | 2009023905 A1 | 2/2009 |
| WO | 2009042977 A1 | 4/2009 |
| WO | 2010030378 A1 | 3/2010 |
| WO | 2010089354 A2 | 8/2010 |
| WO | 2011081626 A1 | 7/2011 |
| WO | 2011113934 A1 | 9/2011 |
| WO | 2012002063 A1 | 1/2012 |
| WO | 2012056365 A2 | 5/2012 |
| WO | 2012087807 A2 | 6/2012 |
| WO | 2012087811 A2 | 6/2012 |
| WO | 2012087816 A2 | 6/2012 |
| WO | 2012087819 A2 | 6/2012 |
| WO | 2012099965 A2 | 7/2012 |
| WO | 2012141752 A2 | 10/2012 |
| WO | 2013110602 A1 | 8/2013 |
| WO | 2013138451 A1 | 9/2013 |
| WO | 2014039673 A1 | 3/2014 |

OTHER PUBLICATIONS

Chargepoint, Inc.; -chargepoin+®; product brochure; 4 pgs.; © 2014; retrieved Mar. 12, 2014 from the internet: http://www.chargepoint.com/network/.

Dixon, Jr.; Eddy current losses in transformer windings and circuit wiring; Unitrode Corp. Seminar Manual (SEM600); Watertown, MA; 12 pgs.; 1988 (year of pub. sufficiently earlier than effective US filing date and any foreign priority date).

Evatran; PluglessTM Level 2 EV Charging System (3.3kW); product brochure; 7 pgs.; retrieved Mar. 12, 2014 from the internet: http://www.pluglesspower.com/tech-specs/.

Ferret, B.; Electric vehicles get big boost!; Renewable Energy World; 3 pgs.; Jul. 30, 2012; retrieved Jul. 30, 2012 from the internet: http://www.renewableenergyworld.com/rea/blog/post/2012/07/.

Motavalli, Jim; WiTricity Takes Its Car-Charging Technology Out for a Road Test; New York Times; 3 pgs.; Jul. 25, 2012; retrieved Mar. 12, 2014 from the internet: http://wheels.blogs.nytimes.com/2012/07/25/witricity-takes-its-car-charging-technology-out-for-a-road-test/.

Notification of Transmittal of the International Search Report and the Written Opinion of the International Searching Authority for PCT Application No. PCT/US2015/051474, dated Dec. 30, 2015.

Development and Implementation of RFID Technology, Ed. Cristina Turcu, Feb. 2009, pp. 28-30, 93-97.

Merli, Francesco, et al., "Design, Realization and Measurements of a Miniature Antenna for Implantable Wireless Communication Systems", IEEE Transaction on Antennas and Propagation, vol. 59, No. 10, Oct. 2011, pp. 3544-3555.

Merli, Francesco, et al., "The Effect of Insulating Layers on the Performance of Implanted Antennas", IEEE Transaction on Antennas and Propagation, vol. 59, No. 1, Jan. 2011, pp. 21-31.

Abadia, Javier, et al., 3D-Spiral Small Antenna Design and Realization for Biomdical Telemetry in the MICS Band. Radioengineering, vol. 18, No. 4, Dec. 2009, pp. 359-367.

* cited by examiner $$k \approx \frac{A_2}{A_1} \cos\theta$$

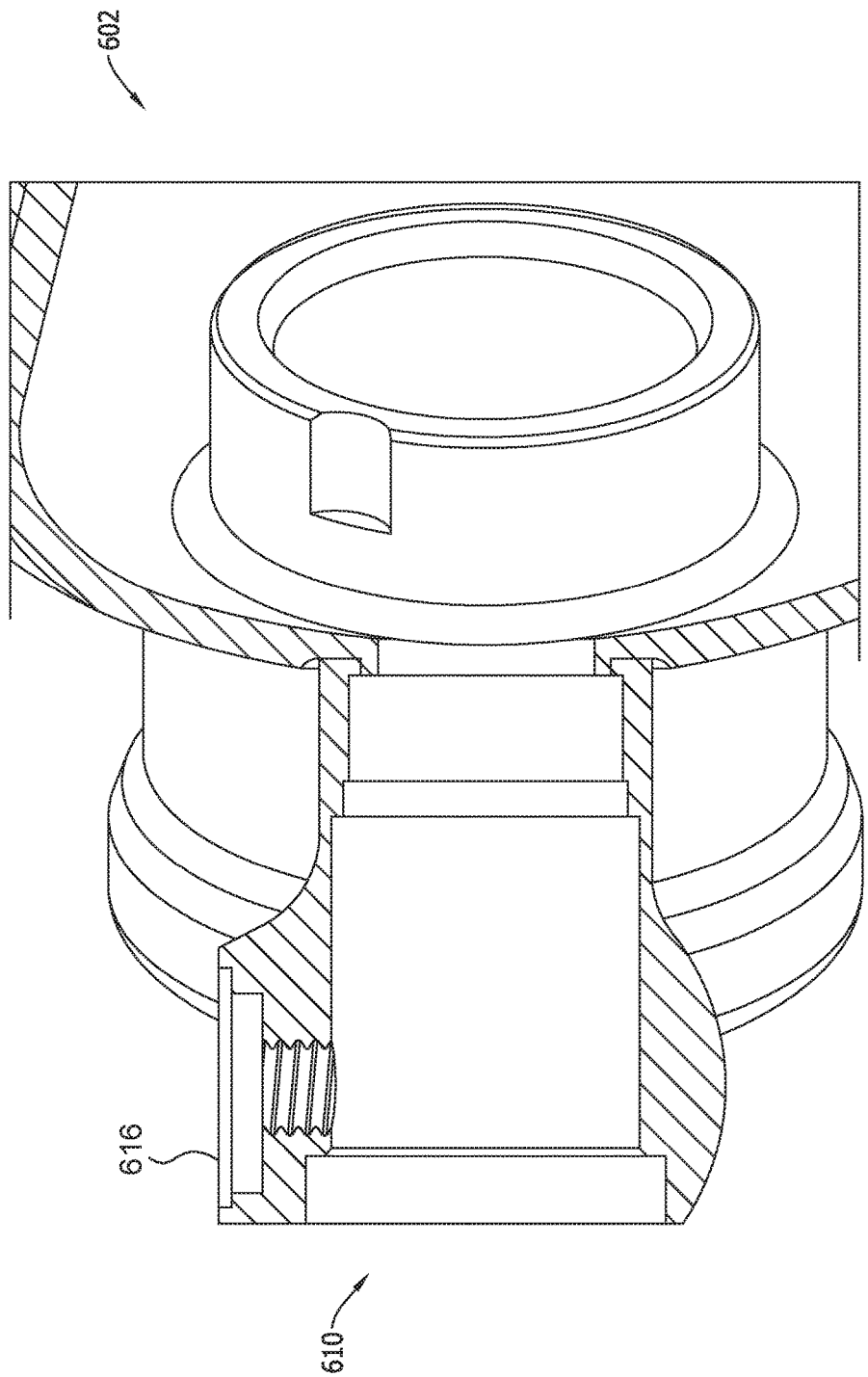

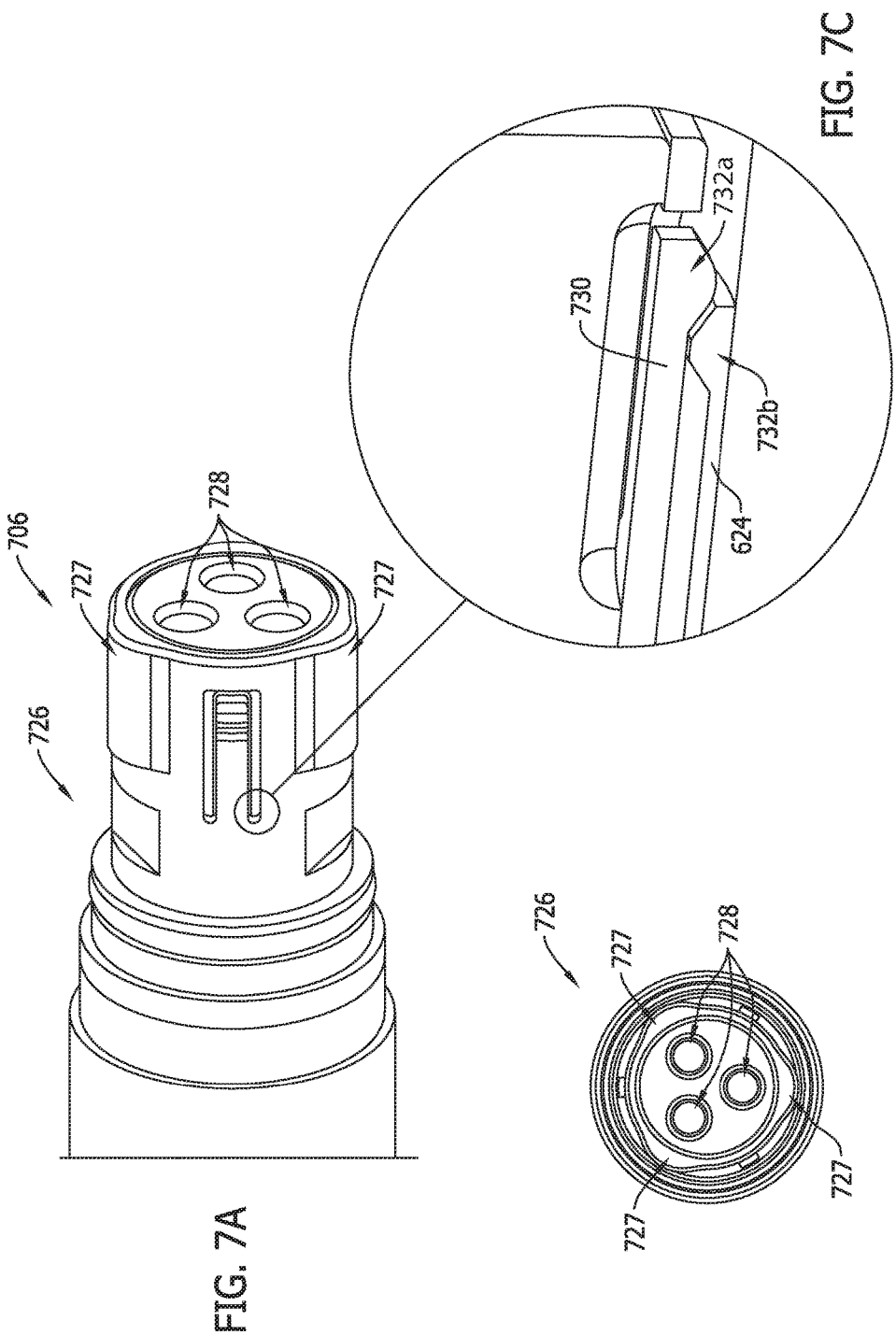

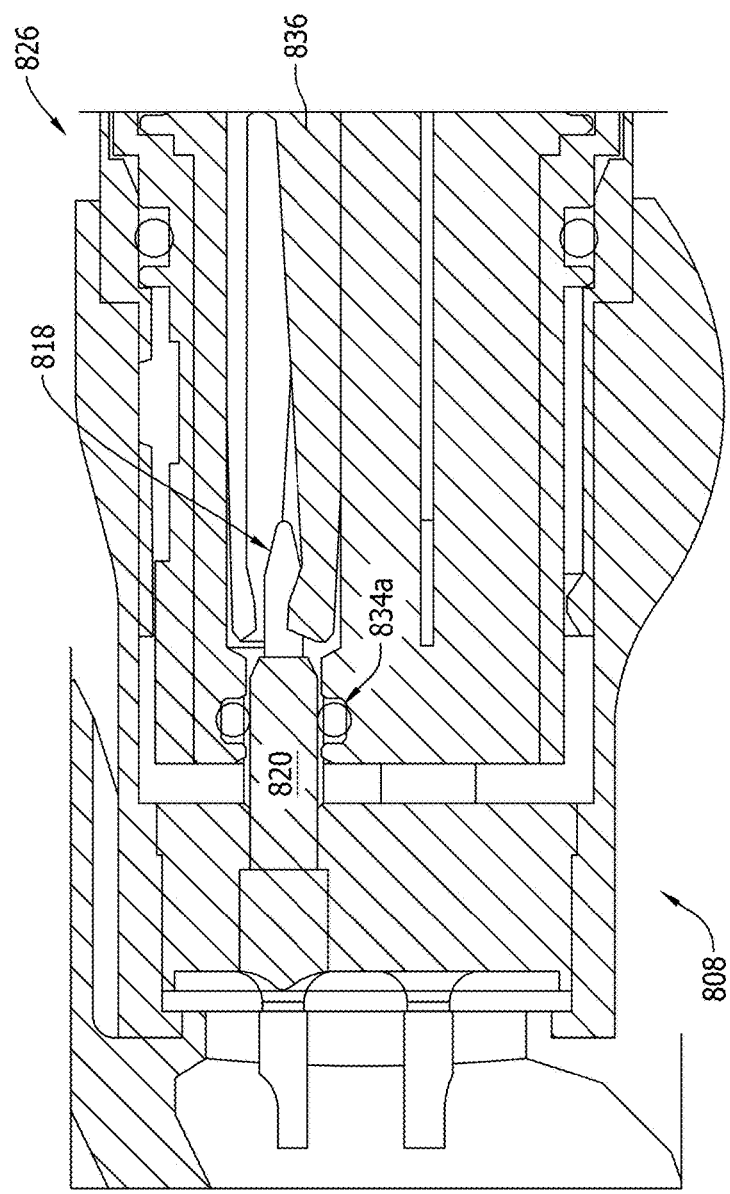

MULTIAXIAL CONNECTOR FOR IMPLANTABLE DEVICES

CROSS-REFERENCE TO RELATED APPLICATIONS

This application is a divisional of U.S. application Ser. No. 14/876,554 (now U.S. Pat. No. 9,583,874), titled "Multiaxial Connector for Implantable Devices", filed on Oct. 6, 2015, which claims the benefit of U.S. Provisional Appln. No. 62/060,435, titled "Multiaxial Connector for Implantable Devices", filed on Oct. 6, 2014, both of which are incorporated herein by reference in their entirety.

INCORPORATION BY REFERENCE

All publications and patent applications mentioned in this specification are herein incorporated by reference to the same extent as if each individual publication or patent application was specifically and individually indicated to be incorporated by reference.

FIELD

Embodiments of the invention relate to wireless energy transfer, and more specifically, to electrical connections between implanted devices including implanted devices that transfer energy from a power source outside the body to an implanted medical device inside the body.

BACKGROUND

Various techniques have been developed to transfer energy wirelessly, and in some cases over long distances. Examples of such systems include U.S. Pat. Nos. 6,327,504; 6,772,011; 7,825,543; and 8,076,801 and U.S. Pub. Nos. 2010/0102639 and 2010/010909445, the entire contents of which are incorporated herein for all purposes by reference.

More recently, there has been development into powering an implanted device wirelessly with a Transcutaneous Energy Transfer (TET) system. Many implantable medical devices require power sources or electrical systems to power the implant. Typically this is achieved using transcutaneous wiring to connect a power source to the implant. TET systems are designed to replace or supplement the transcutaneous wires.

TET systems typically include a lot of hardware and components. One example of a TET system includes the transmission of energy from a transmit coil to a receive coil using an oscillating magnetic field. The TET system also includes a power supply (e.g., battery and/or power conditioner to connect to AC mains) and processing electronics (e.g., solid state electronics and a controller), and other components. It can be burdensome for a patient to carry all these components, in particular for life-saving devices which must be carried at all times. Furthermore, TET systems often require precise alignment of components. Accordingly, there is a need for improvements to peripherals for carrying the necessary system components.

There is also the need for improved utilization and positioning of TET components. Modern medical devices typically require maximal power efficiency. For example, pumps such as ventricular assist devices (VAD) require a relatively high level of sustained and continuous power. With the advances of medical technology, there are an increasing number of implanted medical devices which can benefit from improvements in wireless energy transmission. Improvements in power usage can translate to meaningful reductions in the form factor of the internal power storage (e.g., battery). Improvements in power transmission can also lead to improvements in operation. For example, a slight improvement in power efficiency can mean significant increases in run time on the battery thus improving patient quality of life (QoL).

TET systems by their nature are sensitive to changes in the system. Even small relative changes to the relative orientation between the transmit and receive coil—distance or angle—can lead to a dramatic increase or decrease in power transmission. Indeed, many modern TET systems can only withstand a separation distance on the order of millimeters and require the coils to be generally in desired alignment. Any deviations can drop the power transmission efficiency below acceptable levels. Some existing TET systems for implantable medical devices require the implanted receiver coil to be positioned just under the skin, and typically include a mechanical feature to maintain exact alignment between the receive and transmit coils. However, by implanting these devices directly under the skin, the size and power requirements of these implanted devices is limited if they are to be powered by a TET system. Moreover, many TET systems are system to changes even within an operational range. For example, if one coil is moving or vibrating rapidly with respect to the other coil the power efficiency will drop dramatically.

The lack of effective positioning systems means that many TET systems are designed for placement of the transmit and receive coils directly adjacent each other in the pectoral region. The pectoral region is known to be relatively stable during activity due to the minimal amount of soft tissue and fat. There is less variability from patient to patient. In part for this reason the pectoral region is a common placement for implantable cardioverter defibrillators (ICD).

Accordingly, there is a need for devices and methods for addressing these and other problems. There is a need for systems and methods that reduce the burden on the patient and improve power transmission. There is the need for improvements to wearable devices for use with wireless energy transfer systems, and in certain respects TET systems.

SUMMARY OF THE DISCLOSURE

The present invention relates to a wireless energy transfer system, and more particularly, to electrical connections for a wireless energy transfer system.

One aspect of the invention relates to a multiaxial connector configured to transfer energy and communications between two or more implanted devices. The multiaxial connector can include a cable-side connector and a device-side connector. The multiaxial connector can include features that ensure reliable operation in challenging implanted environments, including features that prevent corrosion and failure due to the introduction of bodily fluids, and also features that prevent the multiaxial connector from being disconnected.

A multiaxial connector for connecting a first implanted device to a second implanted device is provided, comprising a female driveline cable-side connector, including, a lumen, a platinum iridium tuning fork-shaped connector disposed in the lumen, an o-ring surrounding an interior wall of the lumen, a first cantilevered tactile feedback element, a male device-side connector, including, a platinum iridium electrical pin configured to be inserted into the a platinum iridium tuning fork-shaped connector to make an electrical connection therebetween, a ceramic sheath covering a portion of the platinum iridium electrical pin, the ceramic sheath configure to provide electrical isolation for the platinum iridium pin, the ceramic sheath further being configured to engage the o-ring to prevent fluid from interrupting the electrical connection, a second cantilevered tactile feedback element configured to engage the first cantilevered tactile feedback element so as to provide a user with a tactile response when the electrical connection is made, a locking mechanism configured to secure the female driveline cable-side connector to the male device-side connector.

In some embodiments, the first implanted device comprises a LVAD pump.

In another embodiment, the second implanted device comprises a wireless power receiver.

In one embodiment, the male device-side connector further comprises a pump boss configured to provide an environmentally sealed housing for the platinum iridium electrical pin.

A device-side connector for connecting a first implanted device to a second device with a multi-axial connector is provided, comprising a feed-through assembly configured to provide an electrical connection between the first implanted device and the multi-axial connector, the feed-through assembly comprising three male electrical connectors arranged in a triangular pattern that are configured to be inserted into a corresponding electrical connection of the multi-axial connector at various different angles without the need for a keying feature to guide alignment of the feed-through assembly with the multi-axial connector, a pump boss configured to provide an environmentally sealed housing for the feed-through assembly, and an alignment housing configured align the feed-through assembly with a corresponding electrical connection of the multi-axial connector.

In one embodiment, the pump boss assembly further comprises a locking mechanism configured to secure the multi-axial connector to the pump boss to prevent accidental disconnections.

In some embodiments, the three male electrical connectors comprise platinum iridium.

In another embodiment, the three male electrical connectors are each surrounded by a ceramic material to provide isolation between adjacent electrical connectors.

In some embodiments, the alignment housing comprises one or more tactile feedback elements configured to provide tactile feedback to a user when the multi-axial connector is inserted into the pump boss.

A driveline-side connector of a multi-axial connector for connecting a first implanted device to a second device is provided, comprising three female electrical connectors arranged in a triangular pattern, and a fork-shaped connector disposed inside each of the female electrical connectors, each fork-shaped connector comprising a plurality of tines that include a bump disposed on an inner portion of a distal end of the plurality of tines, the bumps being adapted to provide an improved electrical contact point between the fork-shaped connector and a corresponding male electrical connector of the first implanted device.

In one embodiment, the driveline-side connector further comprises a tactile feedback element configured to provide a user with a tactile feel when the driveline-side connector is inserted into the first implanted device.

In one embodiment, the tactile feedback element is cantilevered.

In another embodiment, the driveline-side connector further comprises alignment features configured to give a user a visual cue for aligning the driveline-side connector with a corresponding device-side connector.

In some embodiments, the alignment features are selected from the group consisting of bumps, detents, or protrusions along a distal portion of the driveline cable-side connector.

In another embodiment, the tactile feedback element comprises a bump configured to interact with a corresponding bump on the first implanted device.

In one embodiment, the fork-shaped connectors comprise platinum iridium.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 6A-6D show various views of a device-side connector of a multiaxial connector. The dimensions shown in the figures are in inches.

FIGS. 7A-7D show various views of the driveline cable-side connector of the multiaxial connector.

FIGS. 8A-8C show various views of the driveline cable-side connector being inserted into the device-side connector.

DETAILED DESCRIPTION

Figure 1:
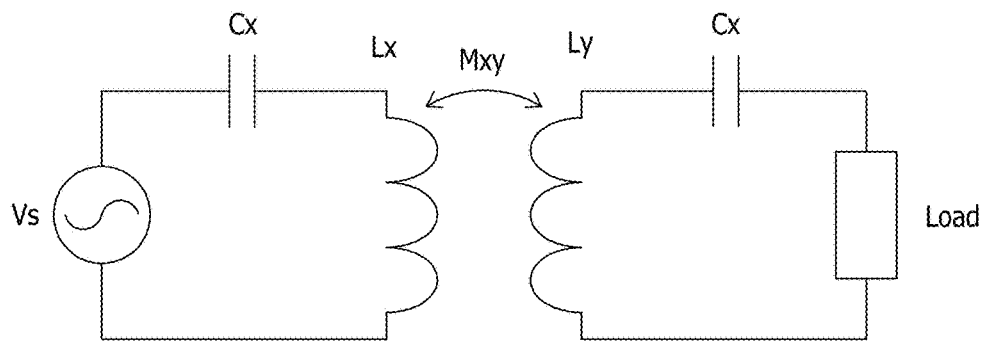
FIG. 1 illustrates a basic wireless energy transfer (WET) system.

In the description that follows, like components have been given the same reference numerals, regardless of whether they are shown in different embodiments. To illustrate an embodiment(s) of the present disclosure in a clear and concise manner, the drawings may not necessarily be to scale and certain features may be shown in somewhat schematic form. Features that are described and/or illustrated with respect to one embodiment may be used in the same way or in a similar way in one or more other embodiments and/or in combination with or instead of the features of the other embodiments.

FIGS. 1-4 illustrate a basic wireless energy transmission (WET) system. The exemplary system is a configured to transmit energy wireless using resonant coils and an oscillating magnetic field.

Various aspects of the system are similar to those described in International Patent Pub. No. WO2013110602; WO2012045050; U.S. Pat. Nos. 8,562,508; 8,140,168; 7,865,245; 7,774,069; 7,711,433; 7,650,187; 7,571,007; 7,741,734; 7,825,543; 6,772,011; 6,591,139; 6,553,263; 6,327,504; and 5,350,413; and U.S. Pub. Nos. 2014/

0028110; 2013/0127253; 2013/0007949; 2010/0308939; 2008/027293; 2007/0123948; 2010/0114143; and 2010/0102639, the entire contents of which patents and applications are incorporated herein for all purposes.

Although important aspects of the inventions are directed to peripherals and wearable devices for a WET system, the design of the devices are typically informed by the performance constraints of the underlying WET system. Accordingly, the basic principles of the WET system will be described below.

Wireless Energy Transfer

With reference to FIG. 1, power may be transmitted wirelessly by magnetic induction. In various embodiments, the transmitter and receiver are closely coupled.

In some cases "closely coupled" or "close coupling" refers to a system that requires the coils to be very near each other in order to operate. For example, in some exemplary cases the external coil is directly adjacent the skin and the internal coil must be implanted subcutaneously just below the external coil.

In some cases "loosely coupled" or "loose coupling" refers to a system configured to operate when the coils have a significant spatial and/or axial separation, and in some cases up to distance equal to or less than the diameter of the larger of the coils. In some cases, "loosely coupled" or "loose coupling" refers a system that is relatively insensitive to changes in physical separation and/or orientation of the receiver and transmitter. In some cases, "loosely coupled" or "loose coupling" refers a highly resonant system and/or a system using strongly-coupled magnetic resonators.

In various embodiments, the transmitter and receiver are non-resonant coils. For example, a change in current in one coil induces a changing magnetic field. The second coil within the magnetic field picks up the magnetic flux, which in turn induces a current in the second coil. An example of a closely coupled system with non-resonant coils is described in International Pub. No. WO2000/074747, incorporated herein for all purposes by reference. A conventional transformer is another example of a closely coupled, non-resonant system. In various embodiments, the transmitter and receiver are resonant coils. For example, one or both of the coils is connected to a tuning capacitor or other means for controlling the frequency in the respective coil. Exemplars of closely coupled system with resonant coils is described in International Pub. Nos. WO2001/037926; WO2012/087807; WO2012/087811; WO2012/087816; WO2012/087819; WO2010/030378; and WO2012/056365, U.S. Pub. No. 2003/0171792, and U.S. Pat. No. 5,350,413 (now abandoned), incorporated herein for all purposes by reference.

In the following description and claims, the terms "coupled" along with its derivatives, may be used. It should be understood that the term "coupled" is used to indicate that two or more elements, which may or may not be in direct physical or electrical contact with each other, cooperate or interact with each other. The terms "energy transfer," "power transfer," and "power transmission," and their derivatives, are used interchangeably and refers to the transmission of energy between two devices.

In various embodiments, the transmitter and receiver are loosely coupled. For example, the transmitter can resonate to propagate magnetic flux that is picked up by the receiver at relatively great distances. In some cases energy can be transmitted over several meters. In a loosely coupled system power transfer may not necessarily depend on a critical distance. Rather, the system may be able to accommodate changes to the coupling coefficient between the transmitter and receiver. An example of a loosely coupled system is described in International Pub. No. WO2012/045050, incorporated herein for all purposes by reference.

Power may be transmitted wirelessly by radiating energy. In various embodiments, the system comprises antennas. The antennas may be resonant or non-resonant. For example, non-resonant antennas may radiate electromagnetic waves to create a field. The field can be near field or far field. The field can be directional. Generally far field has greater range but a lower power transfer rate. An example of such a system for radiating energy with resonators is described in International Pub. No. WO2010/089354, incorporated herein for all purposes by reference. An example of such a non-resonant system is described in International Pub. No. WO2009/018271, incorporated herein for all purposes by reference. Instead of antennas, the system may comprise a high energy light source such as a laser. The system can be configured so photons carry electromagnetic energy in a spatially restricted, direct, coherent path from a transmission point to a receiving point. An example of such a system is described in International Pub. No. WO2010/089354, incorporated herein for all purposes by reference.

Power may also be transmitted by taking advantage of the material or medium through which the energy passes. For example, volume conduction involves transmitting electrical energy through tissue between a transmitting point and a receiving point. An example of such a system is described in International Pub. No. WO2008/066941, incorporated herein for all purposes by reference.

Power may also be transferred using a capacitor charging technique. The system can be resonant or non-resonant. Exemplars of capacitor charging for wireless energy transfer are described in International Pub. No. WO2012/056365, incorporated herein for all purposes by reference.

The system in accordance with various aspects of the invention will now be described in connection with a system for wireless energy transfer by magnetic induction. The exemplary system utilizes resonant power transfer. The system works by transmitting power between the two inductively coupled coils. In contrast to a transformer, however, the exemplary coils are not coupled together closely. A transformer generally requires the coils to be aligned and positioned directly adjacent each other. The exemplary system accommodates looser coupling of the coils.

While described in terms of one receiver coil and one transmitter coil, one will appreciate from the description herein that the system may use two or more receiver coils and two or more transmitter coils. For example, the transmitter may be configured with two coils—a first coil to resonate flux and a second coil to excite the first coil. One will further appreciate from the description herein that usage of "resonator" and "coil" may be used somewhat interchangeably. In various respects, "resonator" refers to a coil and a capacitor connected together.

In general, the system in accordance with various embodiments of this disclosure may include any system for wireless transmitting energy over a distance. The system generally includes one or more components for transmitting and receiving the energy. The energy may take various forms such as an electromagnetic field.

With reference to FIGS. 1-4, the exemplary system comprises one or more transmitters configured to transmit power wirelessly to one or more receivers. In various embodiments, the system includes a transmitter and more than one receiver in a multiplexed arrangement. A frequency generator may be electrically coupled to the transmitter to drive the transmitter to transmit power at a particular frequency or range of frequencies. The frequency generator can include a voltage controlled oscillator and one or more switchable arrays of capacitors, a voltage controlled oscillator and one or more varactors, a phase-locked-loop, a direct digital synthesizer, or combinations thereof. The transmitter can be configured to transmit power at multiple frequencies simultaneously. The frequency generator can include two or more phase-locked-loops electrically coupled to a common reference oscillator, two or more independent voltage controlled oscillators, or combinations thereof. The transmitter can be arranged to simultaneously delivery power to multiple receivers at a common frequency.

In various embodiments, the transmitter is configured to transmit a low power signal at a particular frequency. The transmitter may transmit the low power signal for a particular time and/or interval. In various embodiments, the transmitter is configured to transmit a high power signal wirelessly at a particular frequency. The transmitter may transmit the high power signal for a particular time and/or interval.

In various embodiments, the receiver includes a frequency selection mechanism electrically coupled to the receiver coil and arranged to allow the resonator to change a frequency or a range of frequencies that the receiver can receive. The frequency selection mechanism can include a switchable array of discrete capacitors, a variable capacitance, one or more inductors electrically coupled to the receiving antenna, additional turns of a coil of the receiving antenna, or combinations thereof.

In general, most of the flux from the transmitter coil does not reach the receiver coil. The amount of flux generated by the transmitter coil that reaches the receiver coil is described by "k" and referred to as the "coupling coefficient."

In various embodiments, the system is configured to maintain a value of k in the range of between about 0.2 to about 0.01. In various embodiments, the system is configured to maintain a value of k of at least 0.01, at least 0.02, at least 0.03, at least 0.04, or at least 0.05.

In various embodiments, the coils are physically separated. In various embodiments, the separation is greater than a thickness of the receiver coil. In various embodiments, the separation distance is equal to or less than the diameter of the larger of the receiver and transmitter coil.

Because most of the flux does not reach the receiver in the exemplary system, the transmitter coil must generate a much larger field than what is coupled to the receiver. In various embodiments, this is accomplished by configuring the transmitter with a large number of amp-turns in the coil.

Since only the flux coupled to the receiver gets coupled to a real load, most of the energy in the field is reactive. The current in the coil can be sustained with a capacitor connected to the coil to create a resonator. The power source thus only needs to supply the energy absorbed by the receiver. The resonant capacitor maintains the excess flux that is not coupled to the receiver.

In various embodiments, the impedance of the receiver is matched to the transmitter. This allows efficient transfer of energy out of the receiver. In this case the receiver coil may not need to have a resonant capacitor.

FIG. 1 illustrates a simplified circuit for wireless energy transmission (WET). The exemplary system shows a series connection, but the system can be connected as either series or parallel on either the transmitter or receiver side.

The exemplary transmitter includes a coil Lx connected to a power source Vs by a capacitor Cx. The exemplary receiver includes a coil Ly connected to a load by a capacitor Cy. Capacitor Cx may be configured to make Lx resonate at a desired frequency. Capacitance Cx of the transmitter coil may be defined by its geometry. Inductors Lx and Ly are connected by coupling coefficient k. Mxy is the mutual inductance between the two coils. The mutual inductance, Mxy, is related to coupling coefficient, k.

$$Mxy = k\sqrt{Lx \cdot Ly}$$

In the exemplary system the power source Vs is in series with the transmitter coil Lx so it may have to carry all the reactive current. This puts a larger burden on the current rating of the power source and any resistance in the source will add to losses.

The exemplary system includes a receiver configured to receive energy wirelessly transmitted by the transmitter. The exemplary receiver is connected to a load. In an exemplary embodiment, the load an operative element such as an implanted medical device. In various embodiments, the load is one of a rechargeable power source and an operative element. For example, the receiver may be connected to a DC bus which is in turn connected to various components requiring power. These components may include, but are not limited to, a power source (e.g., battery), an operative medical device, a telemetry system, and associated circuitry. The receiver and load may be connected electrically with a controllable switch.

In various embodiments, the receiver includes a circuit element configured to be connected or disconnected from the receiver coil by an electronically controllable switch. The electrical coupling can include both a serial and parallel arrangement. The circuit element can include a resistor, capacitor, inductor, lengths of an antenna structure, or combinations thereof. The system can be configured such that power is transmitted by the transmitter and can be received by the receiver in predetermined time increments.

In various embodiments, the transmitter coil and/or the receiver coil is a substantially two-dimensional structure. In various embodiments, the transmitter coil may be coupled to a transmitter impedance-matching structure. Similarly, the receiver coil may be coupled to a receiver impedance-matching structure. Examples of suitable impedance-matching structures include, but are not limited to, a coil, a loop, a transformer, and/or any impedance-matching network. An impedance-matching network may include inductors or capacitors configured to connect a signal source to the resonator structure.

In various embodiments, the transmitter is controlled by a controller (not shown) and driving circuit. The controller and/or driving circuit may include a directional coupler, a signal generator, and/or an amplifier. The controller may be configured to adjust the transmitter frequency or amplifier gain to compensate for changes to the coupling between the receiver and transmitter.

In various embodiments, the transmitter coil is connected to an impedance-matched coil loop. The loop is connected to a power source and is configured to excite the transmitter coil. The first coil loop may have finite output impedance. A signal generator output may be amplified and fed to the transmitter coil. In use power is transferred magnetically between the first coil loop and the main transmitter coil, which in turns transmits flux to the receiver. Energy received by the receiver coil is delivered by Ohmic connection to the load.

One of the challenges to a practical circuit is how to get energy in and out of the resonators. Simply putting the power source and load in series or parallel with the resonators is difficult because of the voltage and current required. In various embodiments, the system is configured to achieve an approximate energy balance by analyzing the system characteristics, estimating voltages and currents involved, and controlling circuit elements to deliver the power needed by the receiver.

In an exemplary embodiment, the system load power, PL, is assumed to be 15 Watts and the operating frequency of the system, f, is 250 kHz. Then, for each cycle the load removes a certain amount of energy from the resonance:

$$e_L = \frac{P_L}{f} = 60 \text{ μJ}$$ Energy the load removes in one cycle

It has been found that the energy in the receiver resonance is typically several times larger than the energy removed by the load for operative, implantable medical devices. In various embodiments, the system assumes a ratio 7:1 for energy at the receiver versus the load removed. Under this assumption, the instantaneous energy in the exemplary receiver resonance is 420 μJ.

The exemplary circuit was analyzed and the self-inductance of the receiver coil was found to be 60 uH. From the energy and the inductance, the voltage and current in the resonator could be calculated.

$$e_y = \frac{1}{2} Li^2$$

$$i_y = \sqrt{\frac{2e_y}{L}} = 3.74 \text{ A peak}$$

$$v_y = \omega L_y i_y = 352 \text{ V peak}$$

The voltage and current can be traded off against each other. The inductor may couple the same amount of flux regardless of the number of turns. The Amp-turns of the coil needs to stay the same in this example, so more turns means the current is reduced. The coil voltage, however, will need to increase. Likewise, the voltage can be reduced at the expense of a higher current. The transmitter coil needs to have much more flux. The transmitter flux is related to the receiver flux by the coupling coefficient. Accordingly, the energy in the field from the transmitter coil is scaled by k.

$$e_x = \frac{e_y}{k}$$

Given that k is 0.05:

$$e_x = \frac{420 \text{ μJ}}{0.05} = 8.4 \text{ mJ}$$

For the same circuit the self inductance of the transmitter coil was 146 uH as mentioned above. This results in:

$$i_x = \sqrt{\frac{2e_x}{L}} = 10.7 \text{ A peak}$$

$$v_x = \omega L_x i_x = 2460 \text{ V peak}$$

One can appreciate from this example, the competing factors and how to balance voltage, current, and inductance to suit the circumstance and achieve the desired outcome. Like the receiver, the voltage and current can be traded off against each other. In this example, the voltages and currents in the system are relatively high. One can adjust the tuning to lower the voltage and/or current at the receiver if the load is lower.

One can also appreciate from the above that the form factor and weights of the various WET components may depend to a large degree on the WET performance criteria.

Figure 2:
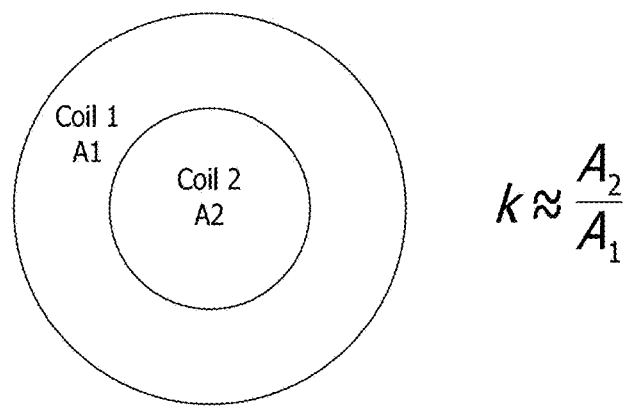
FIG. 2 illustrates the flux generated by a pair of coils.
Figure 3A:
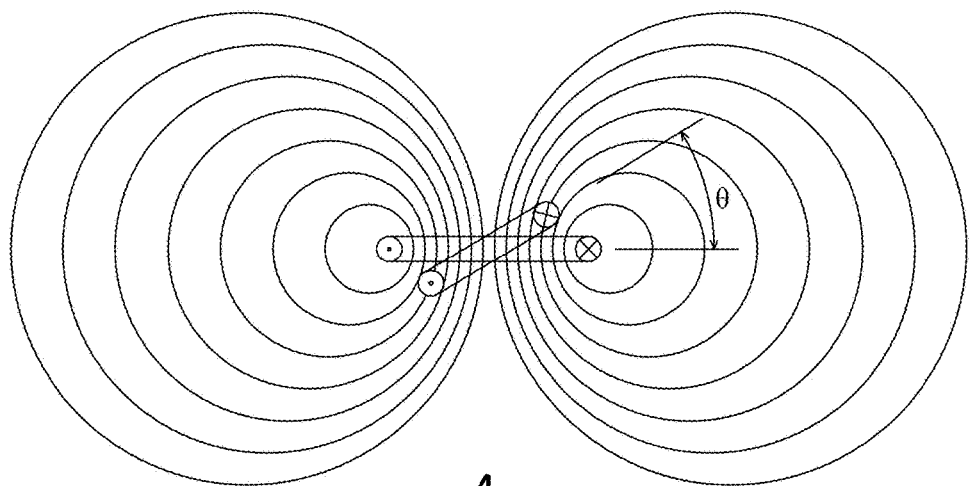
FIGS. 3A and 3B illustrate the effect of coil alignment on the coupling coefficient.
Figure 3B:
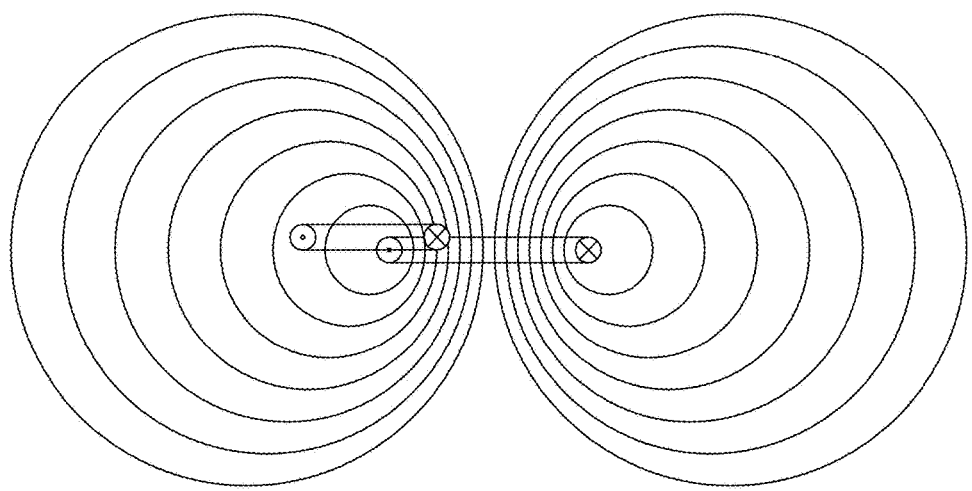

Turning to FIGS. 2, 3A, and 3B, the coupling coefficient and mutual inductance in view of the coil alignment will be explained.

As explained above, the coupling coefficient, k, may be useful for a number of reasons. In one example, the coupling coefficient can be used to understand the arrangement of the coils relative to each other so tuning adjustments can be made to ensure adequate performance. If the receiver coil moves away from the transmitter coil, the mutual inductance will decrease, and ceteris paribus, less power will be transferred. In various embodiments, the system is configured to make tuning adjustments to compensate for the drop in coupling efficiency.

The exemplary system described above often has imperfect information. For various reasons as would be understood by one of skill in the art, the system does not collect data for all parameters. Moreover, because of the physical gap between coils and without an external means of communications between the two resonators, the transmitter may have information that the receiver does not have and vice versa. These limitations make it difficult to directly measure and derive the coupling coefficient, k, in real time.

U.S. Pub. No. 2014/0028110 to Petersen et al., incorporated herein for all purposes by reference, describes several principles for estimating the coupling coefficient, k, for two coils of a given geometry. The approaches may make use of techniques such as Biot-Savart calculations or finite element methods. Certain assumptions and generalizations, based on how the coils interact in specific orientations, are made for the sake of simplicity of understanding. From an electric circuit point of view, all the physical geometry permutations can generally lead to the coupling coefficient.

If two coils are arranged so they are in the same plane, with one coil circumscribing the other, then the coupling coefficient can be estimated to be roughly proportional to the ratio of the area of the two coils. This assumes the flux generated by coil 1 is roughly uniform over the area it encloses as shown in FIG. 2.

If the coils are out of alignment such that the coils are at a relative angle, the coupling coefficient will decrease. The amount of the decrease is estimated to be about equal to the cosine of the angle as shown in FIG. 3A. If the coils are orthogonal to each other such that theta (A) is 90 degrees, the flux will not be received by the receiver and the coupling coefficient will be zero.

If the coils are arranged such that half the flux from one coil is in one direction and the other half is in the other direction, the flux cancels out and the coupling coefficient is zero, as shown in FIG. 3B.

A final principle relies on symmetry of the coils. The coupling coefficient and mutual inductance from one coil to the other is assumed to be the same regardless of which coil is being energized.

$$M_{xy} = M_{yx}$$

In an exemplary embodiment, the WET system is a TET system for an implanted medical device such as a blood pump. Systems and methods are provided herein for wirelessly transmitting power from an external power transmitter to a separate power receiver. The TET systems described herein can be configured to wirelessly transmit power from a transmitter positioned outside of a human body to a receiver implanted within the body. The receiver can be coupled to circuitry and a power source to power and operate an implantable medical device coupled to the receiver.

Figure 4:
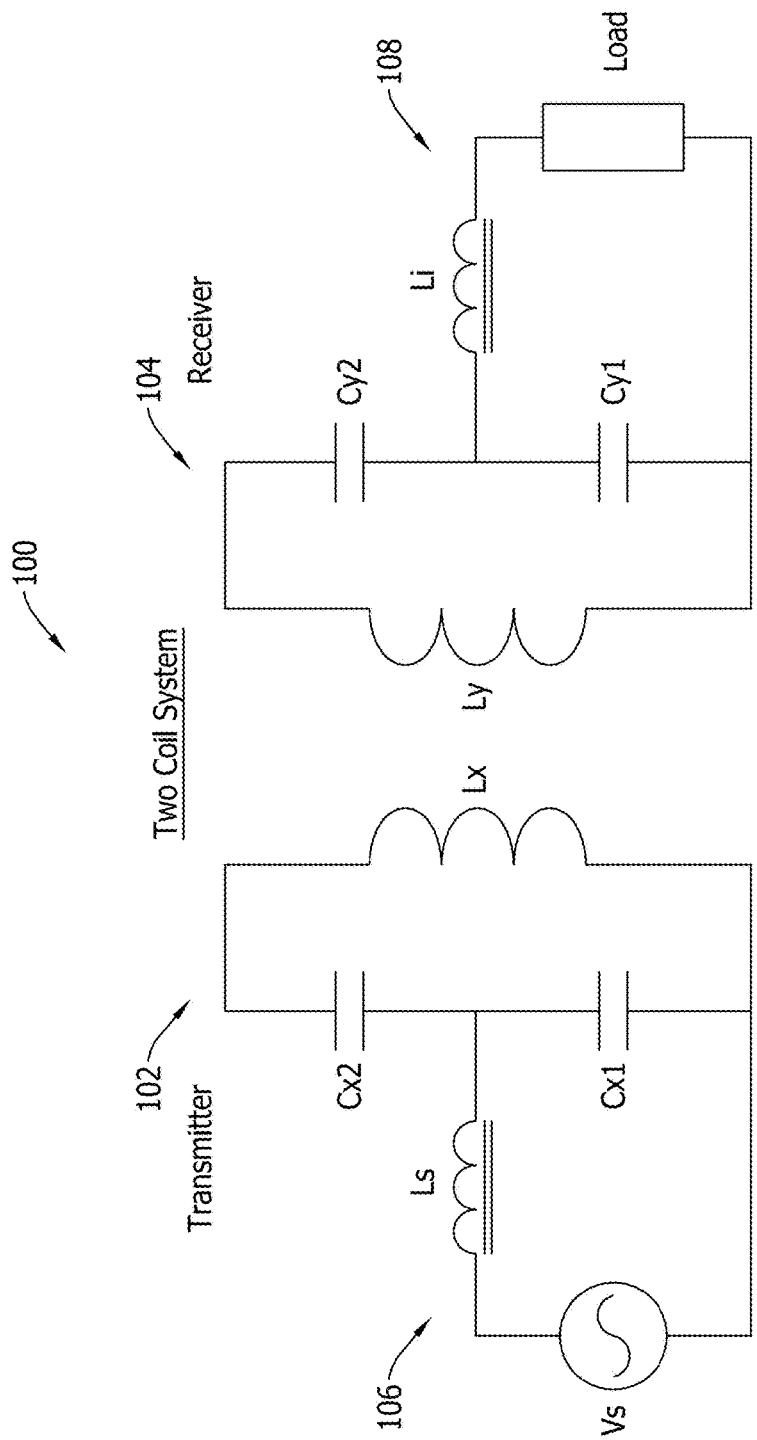
FIG. 4 illustrates half of an exemplary two-coil system for WET having a transmitter and a receiver.

FIG. 4 is an exemplary circuit diagram of half of an exemplary TET circuitry in accordance with the above. In practice the other half of the circuitry mirrors what is shown in FIG. 4. In some embodiments, the resonant systems described herein can operate at high voltages (possibly greater than 1000 Vac rms) to transmit the high power levels required by some implantable applications. For example, power levels of as high as approximately 10 W, 15 W, or more are typically required for a fully implanted LVAD system. In these embodiments, a voltage divider can be used in the TET system so that the load of the receiver resonator and power source of the transmitter resonator can operate at a lower voltage than other parts of the LVAD system. The voltage of the driving circuit and load can be dictated by a battery pack, which is typically in the range of 12-20 Vdc.

In one embodiment shown in FIG. 4, a TET system 100 comprises two resonant systems, a transmitter resonator 102 and a receiver resonator 104. Each of the resonant systems can be connected to a voltage divider circuit. Transmitter resonator 102 includes an inductor Lx and a capacitor Cx2 configured as a tank circuit. Receiver resonator 104 includes an inductor Ly and a capacitor Cy2 configured as a tank circuit. In order to excite each resonant system an impedance matching circuit can connect the transmitter resonator to the power source and the receiver resonator to the load. This way the load and power source only have to supply the real part of the power, and the reactive part of the power is handled by the impedance matching circuit.

In FIG. 4, the impedance matching circuits can comprise voltage dividers formed from capacitors. Voltage divider 106 can be coupled to transmitter resonator 102 and can comprise capacitor Cx1 and inductor Ls, coupled to voltage source Vs. Voltage divider 108 can be coupled to receiver resonator 104 and can comprise capacitor Cy1 and inductor L1, coupled to the Load. An additional inductor may be needed in series with the source and load. In a practical circuit the source is most likely a FET push pull circuit operating as a square wave voltage source. The output of the voltage source should not be placed directly across a capacitor or there will be extremely large currents on the switching transitions.

Many drive circuits are possible in addition to the FET push pull circuit (class-D amplifier). These include variations on resonant power amplifiers (classes B, C, and E) or self resonant circuits such as a Royer oscillator. Linear amplifiers (classes A and A-B) will also work, but will have lower efficiency.

Figure 5:
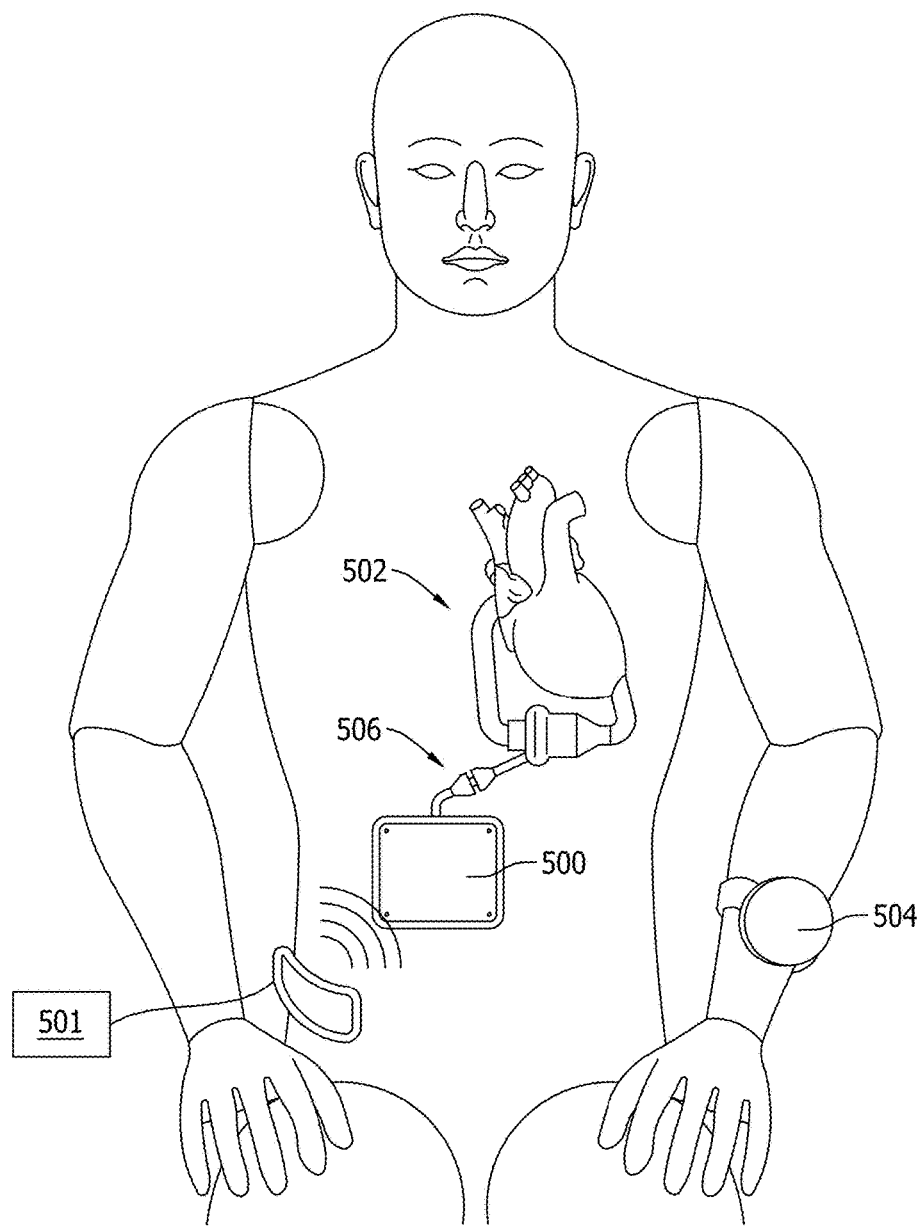
FIG. 5 shows one embodiment of a multiaxial connector.

FIG. 5 illustrates an exemplary wireless power transfer system comprising an implantable TETS receiver unit 500 implanted in an abdomen of a human patient. The receiver unit 500 can be coupled to a device load 502, such as an implantable medical device, e.g., an implantable LVAD or heart pump. The exemplary receiver unit 500 can include a receiver resonator coil and electronics configured to receive wireless energy from an external transmitter 501, which can include a power supply such as a pulse generator connected to a transmitter resonator coil. In one embodiment, the electronics and coils are implanted separately and connected by an implanted cable. In some embodiments, an external controller 504 can be configured to communicate with the TETS receiver 500 and can be worn by the patient, such as on the patient's wrist. In other embodiments, the external controller can be an electronic computing device such as a personal computer, a tablet, smartphone, or laptop computer.

The receiver unit 500 can include a communications system configured to send and receive communications data to and from other electronic devices inside and outside of the body. In one embodiment, the receiver unit further includes an internal rechargeable power source. In various embodiments, the receiver unit 500 of the TET system is configured as a single implanted device including the receive coil, antenna, power source, and associated circuitry. The receiver unit is configured so the implantable medical device can be plugged directly into the unit. The single housing configuration makes implantation easier and faster. Additionally, since there are less implants, and consequently less tunneling in the body and percutaneous defect sites, adverse event risks like bleeding and infection are reduced. One of skill will appreciate from the description herein that various internal components of the system can be bundled together or implanted separately. For example, the internal rechargeable power source can be implanted separately from the receiver unit and connected by a power cable. The antenna assembly, power source, and receive coil can all be configured in separate hermetically sealed housings. International Pub. No. WO2007/053881A1, U.S. Pub. No. 2014/0005466, and U.S. Pat. No. 8,562,508, the entire contents of which are incorporated herein for all purposes by reference, disclose several exemplary configurations.

FIG. 5 also illustrates a multiaxial connector 506 connecting the receiver unit to the device load to provide power, data, and or/control signals from the receiver to the device. The exemplary connector 506 is configured to be placed in a fluid-saturated environment (e.g., in the body). The multiaxial connector can include several components, including a driveline cable extending between the receiver unit and the device, a cable-side connector adapted to provide an electrical connection to one end of the driveline cable, and a device-side connector adapted to provide an electrical connection to the medical device. In some embodiments, a first electrical connector (either male or female) can be disposed on a first end of the driveline cable, and the corresponding electrical connector (either female or male) can be disposed on or near the medical device. For example, the multiaxial connector can comprise a female electrical connector on one end of the driveline cable, and a corresponding male electrical connector on the medical device. The multiaxial connector can include similar electrical connectors on the side of the driveline cable for connecting to a corresponding electrical connector on the receiver unit.

In one embodiment, the implanted receiver is configured to remain inside the patient's body for a minimum of three years, and to serve as the power source and controller for a medical device. The exemplary receiver can supply ~10 VAC, ~14 VAC, ~15 VAC, ~16 VAC, or ~17 VAC to drive the medical device. The connector can allow a clinician to surgically replace the receiver by disconnecting the existing driveline cable from the existing receiver, removing the existing receiver, and reconnecting the same driveline cable to a new receiver without removing the medical device. Similarly, the clinician can surgically replace the cable and/or the medical device while leaving the implanted receiver in place.

Figure 6A:
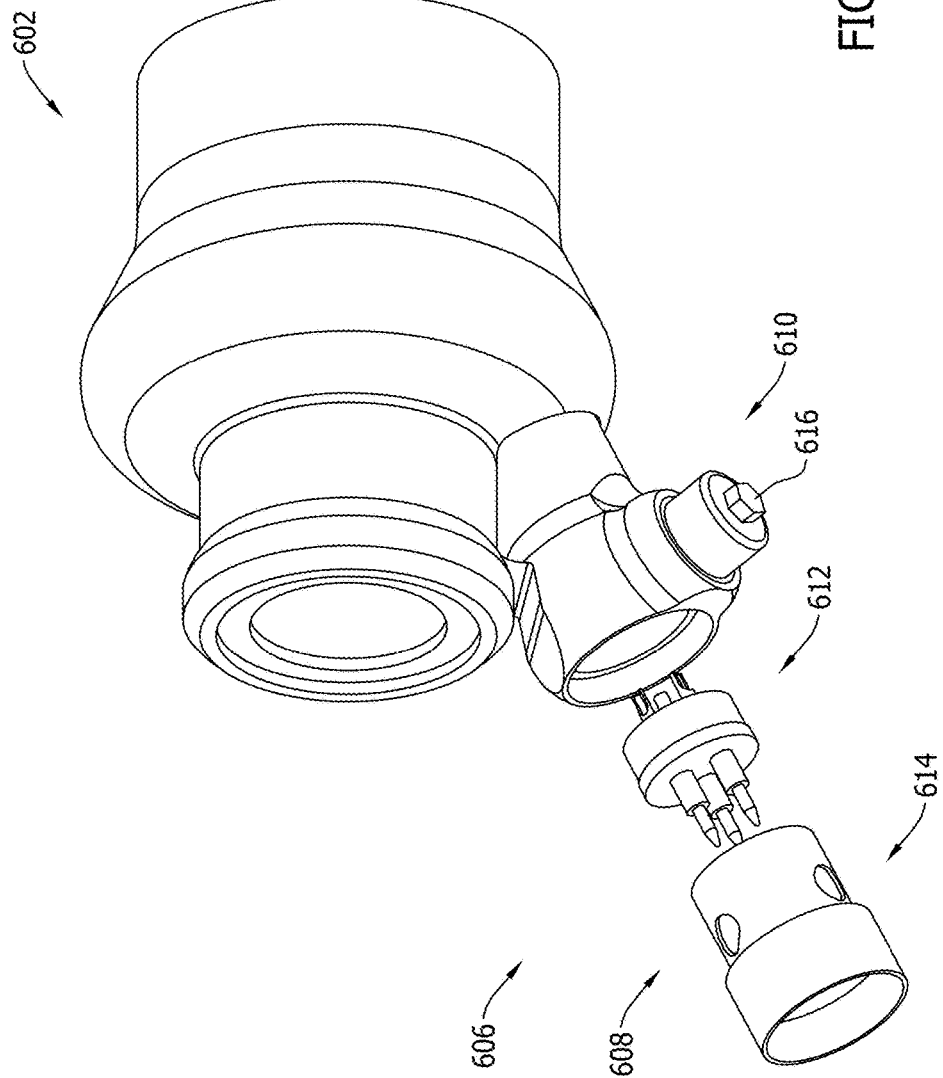

FIG. 6A shows an exploded view of device-side connector 608 of the multiaxial connector 606, for making an electrical connection to the medical device 602, such as to an LVAD pump. The device-side connection 608 can include a pump boss 610, a feed-through assembly 612, and an alignment housing 614. The pump boss 610 can provide an environmentally sealed housing for the feed-through assembly 612, which provides an electrical connection between the multiaxial connector and the device. The alignment housing 614 is configured to align the feed-through assembly 612 with the corresponding electrical connection of the multiaxial connector. The pump boss 610 can also include a locking mechanism 616 configured to secure the multiaxial connector to prevent accidental disconnections, as will be described in more detail below.

In one embodiment, the conductors of the electrical connectors are formed in a symmetric pattern so the female and male ends can be connected at different rotational angles. In the exemplary system, the LVAD pump includes a 3-phase motor so the electrical connector will work if the conductors are inserted into the female ends at various angles. Conventional electrical connectors have 2, 3, or more conductors in a flat configuration. In this case, the male end needs to be inserted into the female end at a particular rotational angle. The exemplary triangular pattern allows the electrical connector to be inserted at three different angles. This eliminates the need for key features to guide alignment of the connector ends.

FIG. 6B shows a cross-sectional view of the pump boss 610 welded to the medical device 602. The cross-sectional view illustrates the dimensions according to one embodiment, and also shows the relative position of the locking mechanism 616 on the pump boss.

Figure 6C:
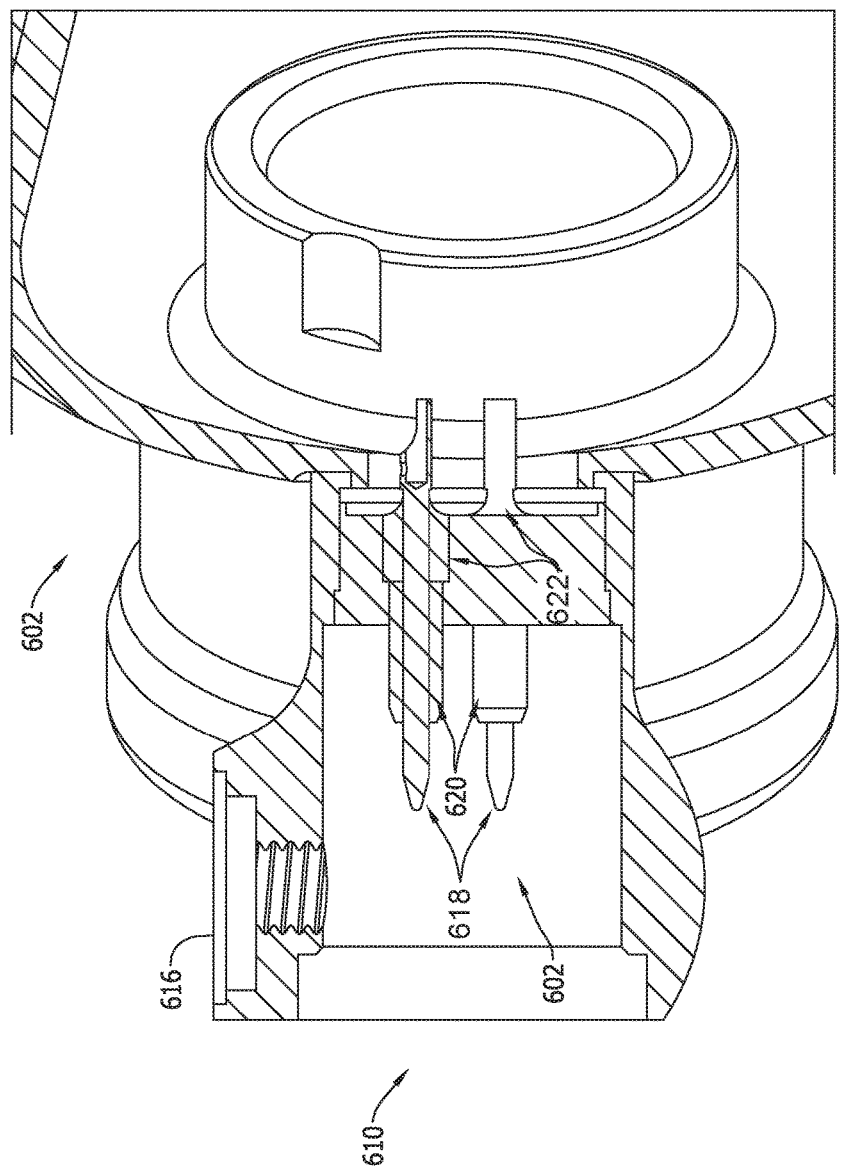

FIG. 6C illustrates the feed-through assembly 612 welded into the pump boss 610. The feed-through assembly can include a plurality of electrical pins 618, which can comprise a conductor. The electrical pins in this embodiment are male electrical connectors. In one specific embodiment, the electrical pins comprise platinum iridium (Pt—Ir) or a PT-Ir alloy (referred to interchangeably herein). As shown in FIG. 6C, a portion of the electrical pins 618 can be surrounded by a ceramic material 620, such as alumina, to provide isolation between the different electrical pins. Also as shown, the feed-through assembly can include a flex material 622 at the base of the electrical pins to allow for some flexing of the pins when the electrical connection is made to the feed-through assembly. FIG. 6C shows one specific embodiment including potential dimensions of the respective components of the feed-through assembly and pump boss.

Figure 6D:
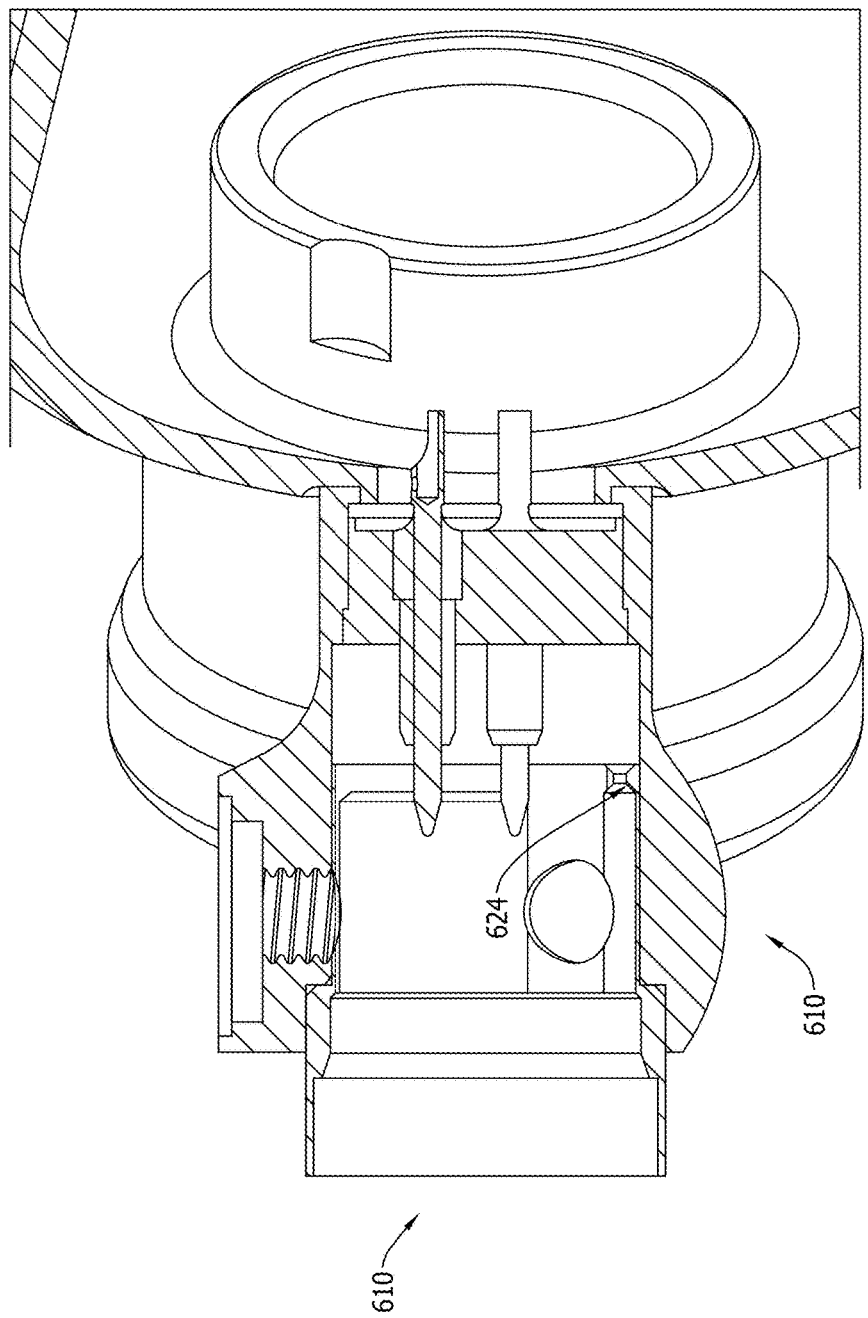

FIG. 6D illustrates the alignment housing 614 welded to the pump boss 610. The alignment housing 614 can include one or more tactile feedback elements 624 configured to provide tactile feedback to a user when the female electrical connector of the driveline cable is inserted into the pump boss to connect to the male electrical connector of the feed-through assembly. As shown in FIG. 6D, the tactile feedback element 624 can comprise a cantilever mechanism with a protruding end. This tactile feedback element can be configured to interact with a corresponding tactile feedback element on the corresponding electrical connector of the driveline cable. This tactile feedback connection will be discussed in more detail below.

The exemplary electrical connectors make use of Pt—Ir by contrast to conventional submersible and implanted connectors. Many existing electrical connectors are formed of stainless steel or similar materials. In the medical field, pacemaker leads, by example, are typically formed of a nickel-cobalt alloy like MP35N. MP35N is selected because of its good corrosion resistance, cost, ease of manufacture, and mechanical properties. However, some applications (e.g., LVADs) have more demanding requirements. Whereas a pacemaker lead is placed in the upper torso, the exemplary connector 606 is positioned in the general abdominal area. As is well known in the art, pacemakers and ICDs are typically located in an epicardial space in the upper torso to lengthen survival of the leads and make them easier to access. In the abdominal area, by contrast, medical devices require open surgery for access to the device. The device is also subjected to strong forces from movement of the anatomy and more easily exposed to fluids which can remain in the connector body during operation thereby leading to failure (e.g., by corrosion). The exemplary connector is configured to resist corrosion at high powers over long periods of time (years). MP35N and other materials may be unsuitable in conditions where the material is exposed to fluid for long periods of time. Pt—Ir has superior corrosion resistance to MP35. In spite of the good corrosion resistance properties of Pt—Ir, however, it has not found common use for electrical connectors in part because of its poor mechanical properties. As will be understood by one of skill from the disclosure herein, the connector in accordance with various embodiments is designed and configured to enable use of Pt—Ir. Moreover, the connector allows use of Pt—Ir for the entire conductor rather than just a small portion. This can be important in applications where a large conductive surface area is needed.

FIGS. 7A-7C show various views of the driveline cable-side connector 726 of the multiaxial connector 706. FIG. 7A shows a side view of the driveline cable-side connector 726, and FIG. 7B shows a top-down view. As shown, this embodiment includes three electrical connectors 728. The electrical connectors can be female electrical connectors adapted to interface with the electrical pins 618 of the header-assembly described above. It should be understood that, depending on the electrical power and communication requirements of the implanted medical device, that some embodiments of the multiaxial connector can include fewer or more than three electrical connections. As is clearly shown in FIGS. 7A-7B, the driveline cable-side connector 726 can include alignment features 727 to give the user a visual cue for aligning the connector during insertion. The alignment features 727 can comprise, for example, bumps, detents, protrusions, or similar mechanisms along a distal portion of the driveline cable-side connector 726.

FIG. 7C shows a close-up view of a tactile feedback element 730 of the driveline cable-side connector 726, which can be configured to engage and interact with a tactile feedback element 624 of the alignment housing described above. Both of the tactile feedback elements can include bumps or protrusions 732a and 732b. When the driveline cable-side connector 726 is inserted into the alignment housing to make a connection between the electrical pins of the device-side connection and the electrical connectors of the driveline cable-side connection, the bump 732a of the tactile feedback element 730 can be advanced past the bump 732b of the tactile feedback element 624. This can provide a tactile feel or click to the user making the connection. In some embodiments, the connection can provide an audible "click". One will appreciate that the exemplary design allows the ramp angles of the bumps 732a and 732b to be designed to provide desired, optimized insertion and removal forces. For example, adjusting the ramp angles of the bumps can provide insertion forces different than the removal forces.

Figure 7D:
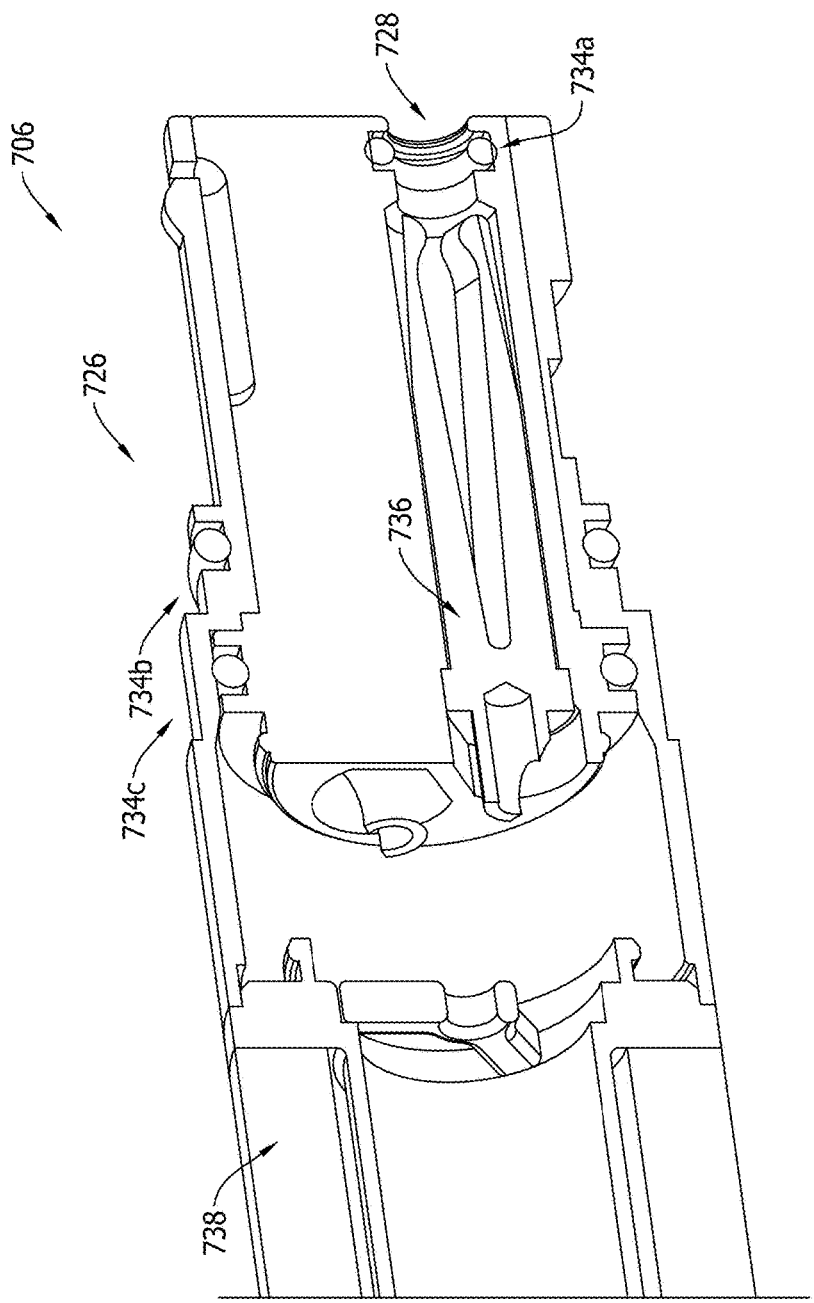

FIG. 7D shows a cross-sectional view of the driveline cable-side connector 726 of the multiaxial connector 706. The driveline cable-side connector 726 can include a plurality of o-rings 734a-734c, positioned in both the interior and exterior of the connector. As shown in FIG. 7D, o-ring 734a can be positioned at the entrance of the electrical connector 728, o-ring 734b can be positioned along an exterior of the driveline cable-side connector, and o-ring 734c can be positioned inside the driveline cable-side connector to provide additional protection against any fluids that may enter the connector. FIG. 7D also shows additional features of the electrical connector 728. The electrical connector 728 can comprise a female tuning fork connector 736 configured to receive an electrical pin of the header assembly. In some embodiments, the tuning fork connector 736 can comprise platinum iridium. A high flexure bend reliever 738 is also shown, which can allow the driveline cable-side connector 726 to flex and bend during use.

Figure 7E:
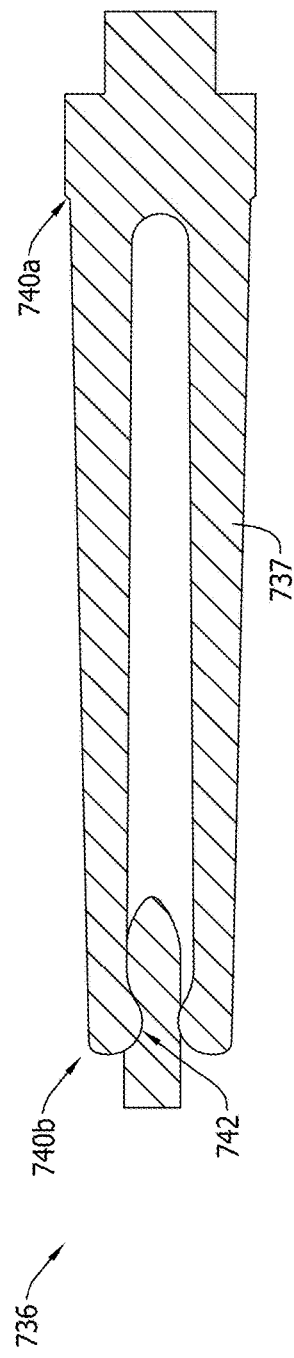
FIGS. 7E-F show schematic diagrams of the tuning fork connector of FIG. 7D. The dimensions shown in the figures are in inches.
Figure 7F:
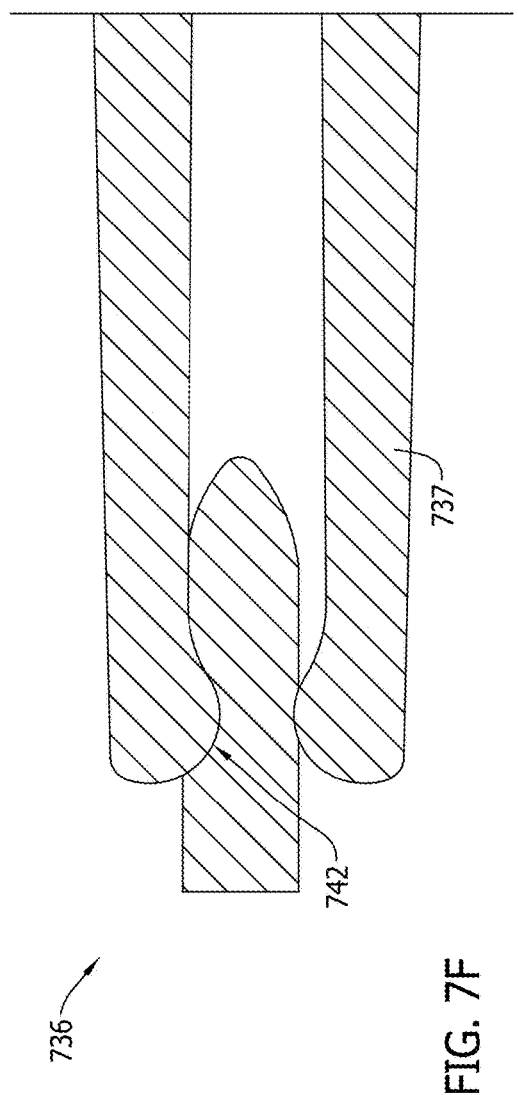

FIGS. 7E-7F show schematic diagrams of the tuning fork connector 736, comprising two or more individual tines 737. As described above, significant challenges are presented when using platinum iridium in a connector or as a spring. In part, Pt—Ir has poor mechanical properties. It has poor ductility and malleability. Accordingly, it is generally unsuitable in conventional connectors where it needs to flex to capture a lead. The tuning fork design of this embodiment overcomes this and other disadvantages. The elongated "tines" or "prongs" extend the length over which the material can flex. The tines also serve to increase the area over which the connector 736 interfaces with the lead, thereby potentially lowering the electrical resistance between these two components.

Referring to FIG. 7E, the tuning fork connector 736 can include a taper along the outside edges of the tines from proximal portion 740a to distal portion 740b. In one particular embodiment, the taper can be optimized for 350-900 grams of pressure between the individual forks 737 of the connector. The tuning fork has been designed so that stress relaxation is not a concern. The individual forks have been optimized to carry the required current with high reliability. The tuning fork connector 736 can also include bumps or protrusions 742 on an inner portion of the distal ends of the individual tines. The bumps 742 can be adapted to provide a better electrical contact point between the tuning fork connector 726 and the male electrical pin inserted into the fork when the connection is made. FIG. 7F is a close-up view of the distal portion of the tuning fork connector, showing the bumps 742 of the individual forks 737 in more detail.

Figure 8A:
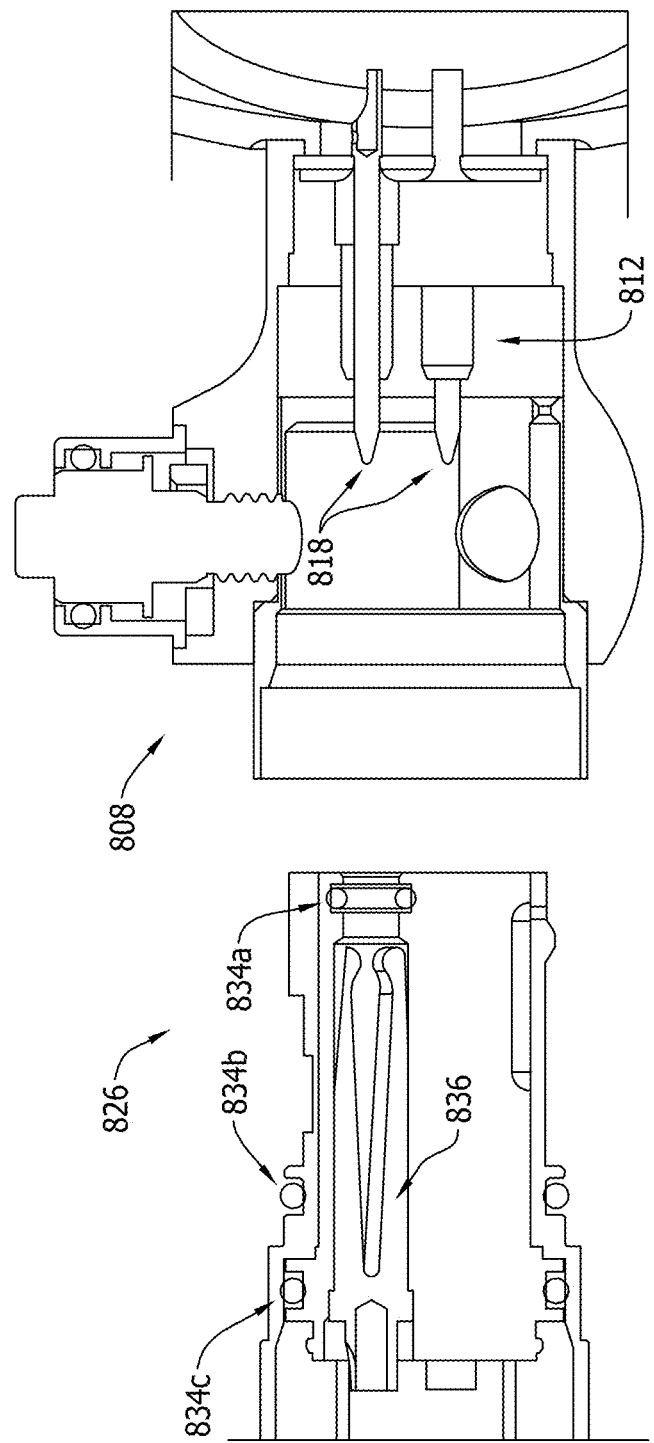
Figure 8C:
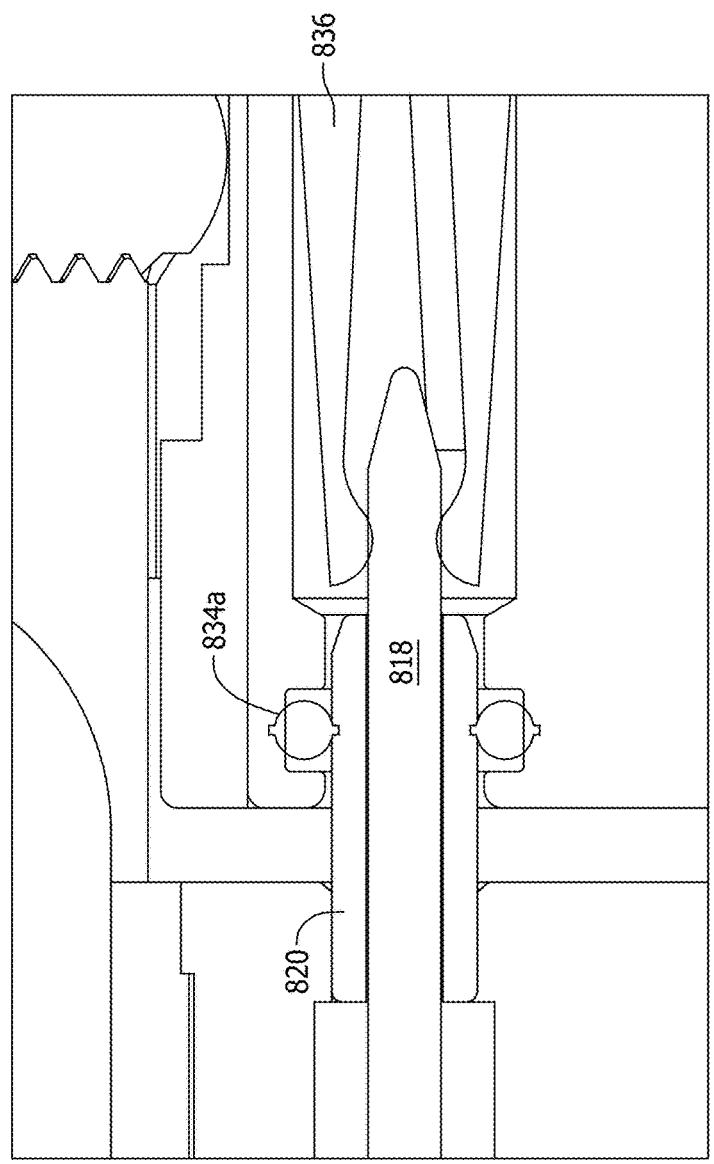

FIGS. 8A-8C show various views of the driveline cable-side connector 826 being inserted into the device-side connector 808. In FIG. 8A, the driveline cable-side connector 826 is separate from the device-side connector 808. The features described above in detail can also be seen, including tuning fork connector 836, o-rings 834a-834c, and feed-through assembly 812 including electrical pins 818.

FIG. 8B is an illustration showing the driveline cable-side connector 826 inserted into the device-side connector 808. In FIG. 8B, ceramic material 820 surrounding electrical pins 818 can sealed with o-ring 834a, to prevent fluid from being introduced into the connection between tuning fork connector 836 and electrical pin 818. FIG. 8C is a close up view of the connection between tuning fork connector 836 and electrical pin 818, which also shows o-ring 834 sealing the interior of the driveline cable-side connector 826 from the environment by surrounding the ceramic material 820 and electrical pin 818.

Figure 9A:
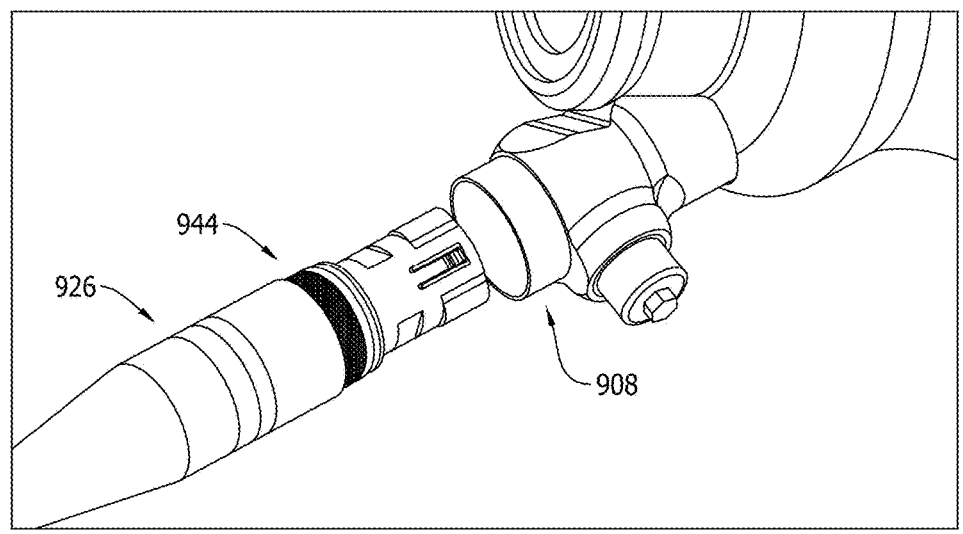
FIGS. 9A-9B show alternative views of the driveline cable-side connector being inserted into the device-side connector.
Figure 9B:
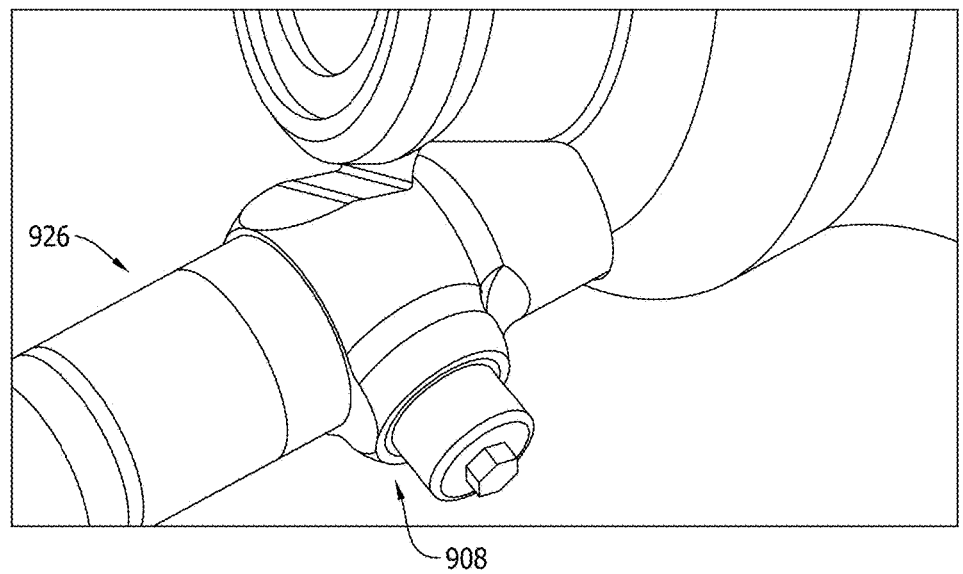

FIGS. 9A-9B show alternative views of the driveline cable-side connector 926 being inserted into the device-side connector 908. In FIG. 9A, the driveline cable-side connector 926 is separated from the device-side connector 908, and in FIG. 9B, the driveline cable-side connector 926 is fully inserted into the device-side connector 908. Also shown in this embodiment, the driveline cable-side connector 926 can include an indicator feature 944 adapted to indicate to a user when the driveline cable-side connector 926 is fully inserted into the device-side connector 908. In FIG. 9A, the indicator feature 944 comprises a visual marking on the connector, such as a dark ring. In FIG. 9B, the driveline cable-side connector 926 is fully inserted into the device-side connector 908 when the indicator feature 944 can no longer be seen. Thus, a user can have a visual marker to confirm that the electrical connection has been made.

Figure 10A:
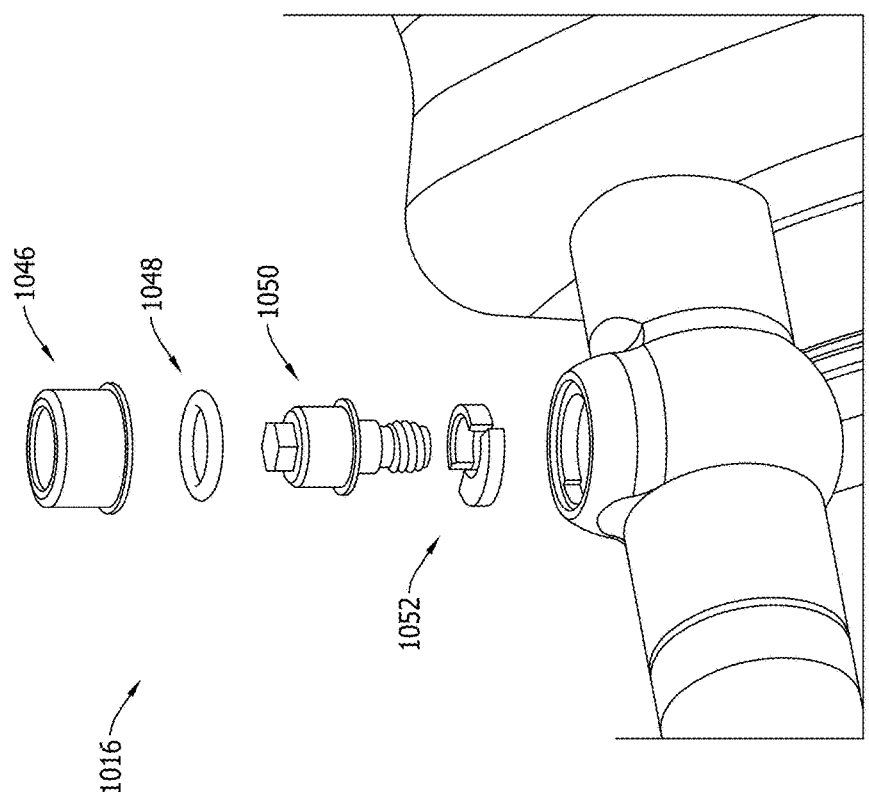
FIGS. 10A-10E show varying views of a locking mechanism of the device-side connector.

FIG. 10A is an exploded view of a locking mechanism 1016, which can be tightened after the connection is made between the driveline cable-side connector and the device-side connector to lock the two connectors together. The locking mechanism can include an external housing 1046, o-ring 1048, screw or bolt 1050, and anti-rotational feature 1052. The o-ring can provide fluid sealing between the screw and the housing, and the anti-rotational feature can be configured to prevent the screw from loosening or unscrewing once the two connectors have been locked together.

Figure 10B:
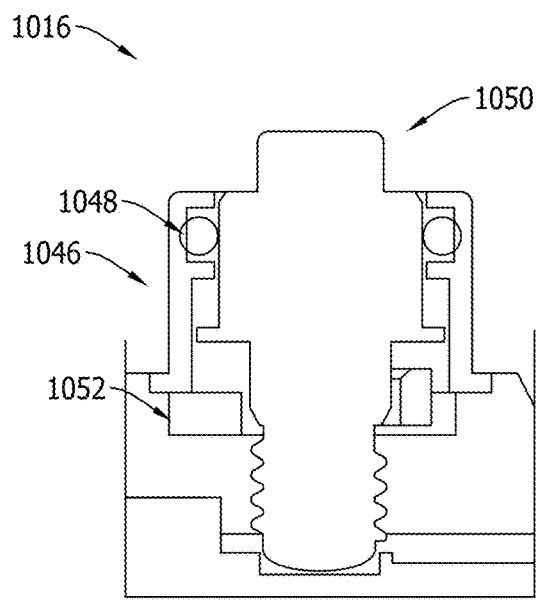
Figure 10C:
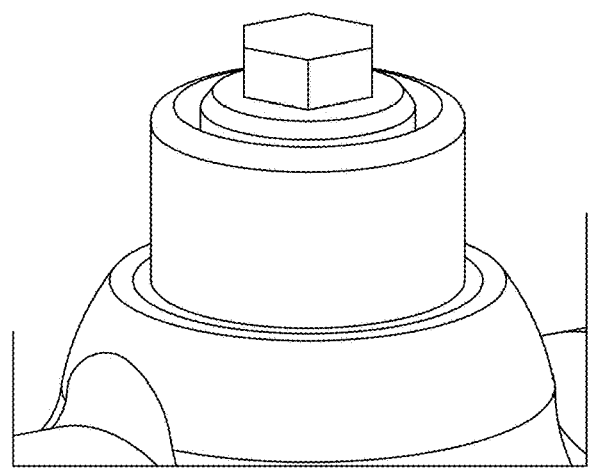

FIG. 10B is a cross-sectional view of the locking mechanism 1016, showing the housing 1046, o-ring 1048, screw or bolt 1050, and anti-rotational feature 1052 joined together and inserted into the device-side connector. FIG. 10C shows an external view of the locking mechanism, showing that the screw 1050 includes a male screw pattern that mates with a female driver to screw in the screw 1050. This male design avoids the use of any holes or depressions which could otherwise promote tissue ingrowth into the locking mechanism.

Figure 10D:
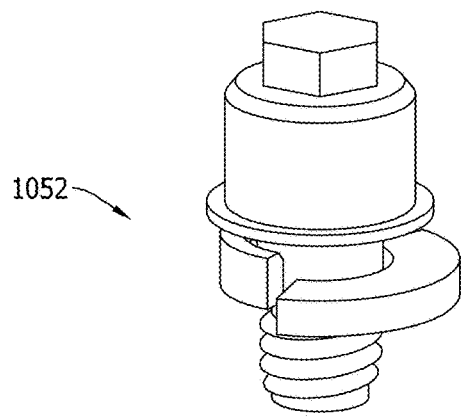

FIG. 10D is another view of the anti-rotational feature 1052. The feature can include two cantilevered-edges that compress when the screw is screwed down upon the anti-rotational feature. This design helps to maintain the screw in position since an increased torque is required to overcome the cantilevered-edges.

Figure 10E:
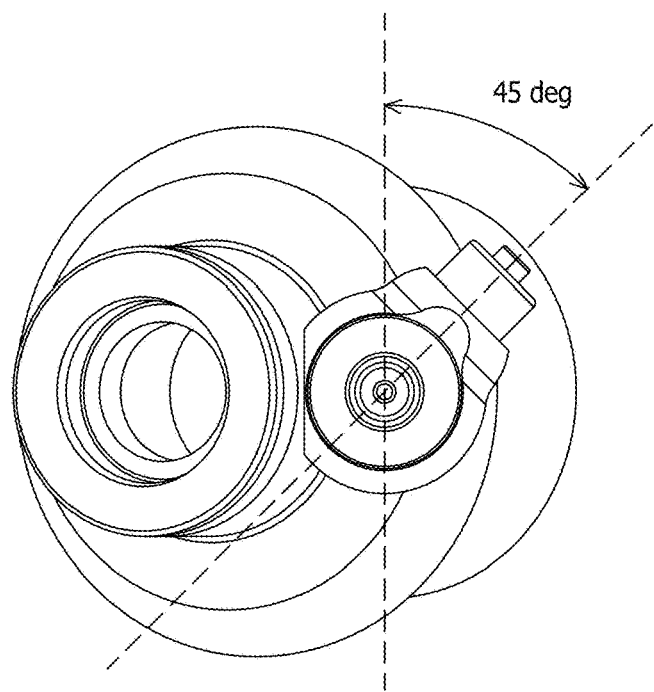

FIG. 10E illustrates how the locking mechanism and the device-side connector can be angled off the implanted device so as to aid in access to the locking mechanism and connector. In one specific embodiment, the locking mechanism can be angled at approximately 45 degrees from a horizontal plane extending through the device.

While the invention has been described in terms of several embodiments, those skilled in the art will recognize that the invention is not limited to the embodiments described, can be practiced with modification and alteration within the spirit and scope of the appended claims. The description is thus to be regarded as illustrative instead of limiting.

What is claimed is:

1. A device-side connector for connecting a first implanted device to a second device with a multi-axial connector, comprising:
   a feed-through assembly configured to provide an electrical connection between the first implanted device and the multi-axial connector, the feed-through assembly comprising exactly three male electrical connectors arranged in a triangular pattern that are configured to be inserted into a corresponding electrical connection of the multi-axial connector, wherein each male electrical connector of the three male electrical connectors is spaced the same distance from the other two electrical connectors, and wherein the triangular pattern enables the three male electrical connectors to be inserted into the corresponding electrical connection at three different rotational angles;

a pump boss configured to provide an environmentally sealed housing for the feed-through assembly; and an alignment housing configured to align the feed-through assembly with the corresponding electrical connection of the multi-axial connector.

2. The device-side connector of claim 1, wherein the pump boss assembly further comprises a locking mechanism configured to secure the multi-axial connector to the pump boss to prevent accidental disconnections.

3. The device-side connector of claim 2, wherein the locking mechanism comprises a screw that threadably engages the pump boss.

4. The device-side connector of claim 3, wherein the locking mechanism further comprises an external housing that surrounds the screw.

5. The device-side connector of claim 4, wherein the locking mechanism further comprises an o-ring that provides fluid sealing between the screw and the external housing.

6. The device-side connector of claim 3, wherein the locking mechanism further comprises an anti-rotational feature that prevents the screw from loosening once the device-side connector is connected to a driveline-side connector.

7. The device-side connector of claim 6, wherein the anti-rotational feature comprises two cantilevered edges that compress when the screw is screwed down upon the anti-rotational feature.

8. The device-side connector of claim 1, wherein the three male electrical connectors comprise platinum iridium.

9. The device-side connector of claim 1, wherein the three male electrical connectors are each surrounded by a ceramic material to provide isolation between adjacent electrical connectors.

10. The device-side connector of claim 1, wherein the alignment housing comprises one or more tactile feedback elements configured to provide tactile feedback to a user when the multi-axial connector is inserted into the pump boss.

11. The device-side connector of claim 1, wherein the feed-through assembly further comprises a flex material at a base of each of the three male electrical connectors.

12. The device-side connector of claim 1, wherein the one or more tactile feedback elements comprise a cantilever mechanism with a protruding end.

* * * * *